US009238609B2

(12) United States Patent
Asthana et al.

(10) Patent No.: US 9,238,609 B2
(45) Date of Patent: Jan. 19, 2016

(54) DICARBOXYLIC ACID MONOMERS AND METHODS OF MAKING AND USING THE SAME

(71) Applicant: SABIC Global Technologies B.V., Bergen op Zoom (NL)

(72) Inventors: Navinchandra Asthana, Sugar Land, TX (US); Kiran Arunkumar Puthamane, Karnataka (IN); Shantaram Narayan Naik, Bangalore (IN); Minor Senthil Kumar, Banglore (IN); Venkata Ramanarayanan Ganapathy Bhotla, Karnataka (IN); Vinodkumar Vasudevan, Kerala (IN); Edward J. Nesakumar, Bangalore (IN); Girish Chandra, Karnataka (IN); Ruud van der Heijden, Roosendaal (NL); Jan Henk Kamps, Bergen op Zoom (NL); Elena Uliyanchenko, Bergen op Zoom (NL); Robert R. Gallucci, Mt. Vernon, IN (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 14/286,024

(22) Filed: May 23, 2014

(65) Prior Publication Data

US 2015/0336869 A1 Nov. 26, 2015

(51) Int. Cl.
| | |
|---|---|
| *C07C 51/265* | (2006.01) |
| *C08G 63/199* | (2006.01) |
| *C08G 63/64* | (2006.01) |
| *C07C 2/72* | (2006.01) |
| *C07C 5/367* | (2006.01) |
| *C07C 1/30* | (2006.01) |
| *C07C 1/207* | (2006.01) |
| *C08K 5/09* | (2006.01) |

(52) U.S. Cl.
CPC ............. *C07C 51/265* (2013.01); *C07C 1/2076* (2013.01); *C07C 1/30* (2013.01); *C07C 2/72* (2013.01); *C07C 5/367* (2013.01); *C08G 63/199* (2013.01); *C08G 63/64* (2013.01); *C07C 2102/08* (2013.01); *C07C 2527/054* (2013.01); *C07C 2531/10* (2013.01)

(58) Field of Classification Search
CPC ...... C07C 51/265; C07C 1/2076; C07C 1/30; C07C 5/367; C08K 5/09
USPC ...................................................... 562/855
See application file for complete search history.

(56) References Cited

U.S. PATENT DOCUMENTS

| | | | |
|---|---|---|---|
| 3,153,008 A | 10/1964 | Fox | |
| 3,265,660 A | 8/1966 | Burgess et al. | |
| 3,539,619 A * | 11/1970 | Steitz, Jr. ............... | C07C 63/337 560/80 |
| 3,577,442 A * | 5/1971 | Holler ................ | C08G 59/4223 528/112 |
| 3,699,160 A * | 10/1972 | Steitz, Jr. ................ | C07C 51/42 562/405 |
| 4,154,775 A | 5/1979 | Axelrod | |
| 5,466,777 A | 11/1995 | Caruso et al. | |
| 8,247,619 B2 | 8/2012 | Mahood | |
| 8,669,315 B2 | 3/2014 | Gallucci et al. | |
| 8,686,075 B2 | 4/2014 | Gallucci et al. | |
| 2007/0276065 A1 | 11/2007 | Barton et al. | |
| 2009/0093573 A1 | 4/2009 | Germroth et al. | |
| 2009/0326107 A1 | 12/2009 | Bittner | |
| 2011/0168657 A1 | 7/2011 | Bittner | |
| 2013/0052381 A1 | 2/2013 | Gallucci et al. | |
| 2013/0053489 A1 | 2/2013 | Gallucci et al. | |

FOREIGN PATENT DOCUMENTS

| | | |
|---|---|---|
| GB | 951932 | 3/1964 |
| KR | 1013584 B1 | 2/2011 |
| WO | WO 90/07533 A1 | 7/1990 |
| WO | WO 2008/140705 A1 | 11/2008 |

OTHER PUBLICATIONS

Akahori et al., "Two-step models to predict binding affinity of chemicals to the human estrogen receptor alpha by three-dimensional quantitative structure-activity relationships (3D-QSARs) using receptor-ligand docking simulation," SAR and QSAR in Environment Research, Aug. 2005, 16(4), 323-337.

Bailin et al., "Public Awareness Drives Market for Safer Alternatives: Bisphenol A Market Analysis Report," Investor Environmental Health Network, Sep. 15, 2008, 37 pages.

Bittner et al., Comment on "Lack of androgenicity and estrogenicity of the three monomers used in Eastman's Tritan™ copolyesters by Osimitz et al. (2012)," Food and Chemical Toxicology, Letter to the Editor, Nov. 2012, 50(11), 4236-4237.

Brzozowski et al., "Molecular basis of agonism and antagonism in the oestrogen receptor," Nature, Oct. 1997, vol. 389, 753-758.

Coleman et al., "QSAR Models of the in vitro Estrogen Activity of Bisphenol A Analogs," QSAR Comb. Sci., Apr. 2003, 22(1), 78-88.

Fang et al., "Structure-Activity Relationships for a Large Diverse Set of Natural, Synthetic, and Environmental Estrogens," Chem. Res. Toxicol., Feb. 2001, 14(3), 280-294.

(Continued)

*Primary Examiner* — Sikarl Witherspoon
(74) *Attorney, Agent, or Firm* — Baker Hostetler LLP

(57) ABSTRACT

Disclosed herein are phenylindane dicarboxylic acid (PIDA) monomers, polymer compositions comprising the PIDA monomers, and methods of preparing PIDA monomers. This abstract is intended as a scanning tool for purposes of searching in the particular art and is not intended to be limiting of the present disclosure.

41 Claims, 3 Drawing Sheets

(56) References Cited

OTHER PUBLICATIONS

Hu et al., "Quantitative structure-activity relationships for estrogen receptor binding affinity of phenolic chemicals," Water Research, 2003, vol. 37, 1213-1222.

Kitamura et al., "Comparative Study of the Endocrine-Disrupting Activity of Bisphenol A and 19 Related Compounds," Toxicological Sciences, Jan. 2005, 84(2), 249-259.

Kobayashi et al., "Prediction of endocrine disrupters based on a new structure-activity relationship for sex and environmental hormones using chemical hardness concept," Chem. Pharm. Bull., Jul. 2001, 49(6), 680-688.

Nose et al., "A docking modelling rationally predicts strong binding of bisphenol A to estrogen-related receptor gamma," Protein & Peptide Letters, 2008, 15(3), 290-296.

Osimitz et al., "Lack of androgenicity and estrogenicity of the three monomers used in Eastman's Tritan™ copolyesters," Food and Chemical Toxicology, Feb. 2012, 50(6), 2196-2205.

Parr et al., "Elementary Wave Mechanisms," Density-Functional Theory of Atoms and Molecules, Oxford University Press, New York, Oxford, 1989, 9 pages.

Saliner et al., "Prediction of estrogenicity: validation of a classification model," SAR and QSAR in Environment Research, Apr. 2006, 17(2), 195-223.

Schultz et al., "Structure—Activity Relationships for Gene Activation Oestrogenicity: Evaluation of a Diverse Set of Aromatic Chemicals," Environmental Toxicology, Feb. 2002, 17(1), 14-23.

Vandenberg et al., "Bisphenol-A and the great divide: a review of controversies in the field of endocrine disruption," Endocrine Reviews, Feb. 2009, 30(1), 75-95.

Welshons et al., "Large effects from small exposures. III. Endocrine mechanisms mediating effects of bisphenol A at levels of human exposure," Endocrinology, Jun. 2006, 147(6 Suppl), S56-69.

Yang et al., "Most Plastic Products Release Estrogenic Chemicals: A Potential Health Problem That Can Be Solved," Environmental Health Perspectives, Jul. 2011, 119(7), 989-996.

* cited by examiner

DICARBOXYLIC ACID MONOMERS AND METHODS OF MAKING AND USING THE SAME

BACKGROUND

Development of alternatives to existing polycarbonates, polyesters and polyestercarbonates that maintain properties (e.g., low cost, low color, high transparency and good melt stability) of the corresponding polymers are of great interest in the plastics industry and for the manufacturing industry. To achieve this, a suitable monomer for polymerization reactions is necessary to produce a polymer with the necessary properties.

Preliminary studies of phenylindane dicarboxylic acid (PIDA) monomers indicate that PIDA could serve as a potential alternate monomer in synthesizing new polymers with the necessary properties. However, traditional synthesis methods of PIDA, which require rigorous reaction condition requirements, for example, use of propylene gas, high pressure, and high temperature, coupled with the lack of chemo-selectivity of PIDA, restricts the scale-up of PIDA in large quantities.

Accordingly, there remains a need for improved, efficient, scalable, and cost effective methods for the synthesis of PIDA, which in turn can be readily used in the production of environmentally-friendly alternatives to existing polycarbonates, polyesters and polyestercarbonates. These needs and other needs are satisfied by the various aspects of the present disclosure.

SUMMARY

The present disclosure relates to phenylindane dicarboxylic acid (PIDA) monomers and methods of making the same. The method for making the PIDA monomers comprises: a) reacting an alkylstyrene under first reaction conditions effective to provide a first reaction product comprising at least one phenylindane; and b) reacting the first reaction product under second reaction conditions effective to provide a second reaction product comprising at least one phenylindane dicarboxylic acid (PIDA) monomer.

The PIDA monomers can be used in the production of polymer compositions exhibiting properties such as low cost, high transparency and good melt stability. The resulting polymer compositions can be used in the manufacture of articles requiring materials with low cost, high transparency, and good melt stability.

In one aspect, the disclosure relates to polymer compositions comprising: repeating units derived from at least one PIDA monomer according to the present disclosure.

In various further aspects, the disclosure relates to thermoplastic compositions comprising the disclosed PIDA monomers.

In various further aspects, the disclosure relates to articles comprising the disclosed compositions.

In a further aspect, the disclosure relates to methods of making the disclosed compositions.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional aspects of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE FIGURES

The accompanying figures, which are incorporated in and constitute a part of this specification, illustrate several aspects and together with the description serve to explain the principles of the disclosure.

DETAILED DESCRIPTION

Figure 1:
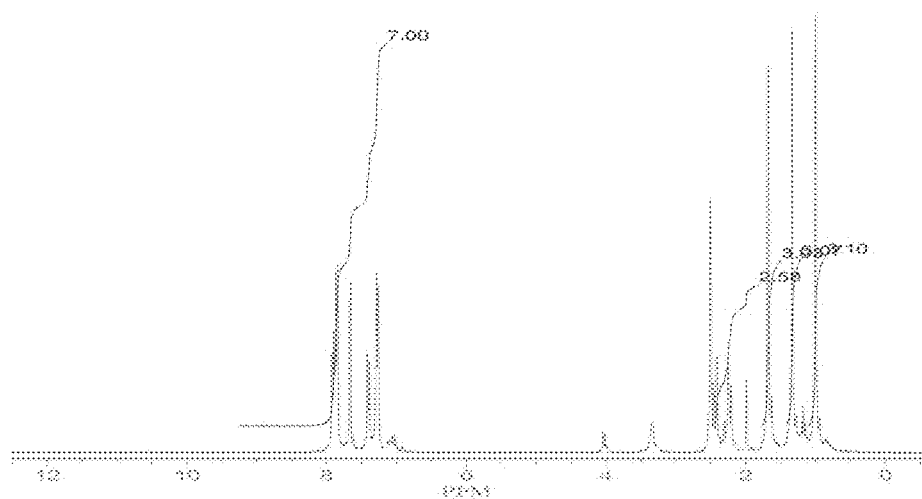
FIG. 1 shows representative NMR data of crude PIDA monomer prepared according to the present disclosure.

The present disclosure can be understood more readily by reference to the following detailed description of the disclosure and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

All publications mentioned herein are incorporated herein by reference to disclose and describe the methods and/or materials in connection with which the publications are cited.

A. Definitions

It is also to be understood that the terminology used herein is for the purpose of describing particular aspects only and is not intended to be limiting. As used in the specification and in the claims, the term "comprising" can include the aspects "consisting of" and "consisting essentially of." Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a polycarbonate polymer" includes mixtures of two or more polycarbonate polymers.

As used herein, the term "combination" is inclusive of blends, mixtures, alloys, reaction products, and the like.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally substituted alkyl" means that the alkyl group can or cannot be substituted and that the description includes both substituted and unsubstituted alkyl groups.

As used herein, the term "effective amount" refers to an amount that is sufficient to achieve the desired modification of a physical property of the composition or material. For example, an "effective amount" of a filler refers to an amount that is sufficient to achieve the desired improvement in the property modulated by the formulation component, e.g. achieving the desired level of modulus. The specific level in terms of wt % in a composition required as an effective amount will depend upon a variety of factors including the amount and type of polycarbonate, amount and type of polycarbonate, amount and type of thermally conductive filler, and end use of the article made using the composition.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

Compounds are described using standard nomenclature. For example, any position not substituted by any indicated group is understood to have its valence filled by a bond as indicated, or a hydrogen atom. A dash ("-") that is not between two letters or symbols is used to indicate a point of attachment for a substituent. For example, —CHO is attached through carbon of the carbonyl group. Unless defined otherwise, technical and scientific terms used herein have the same meaning as is commonly understood by one of skill in the art to which this disclosure belongs.

The term "alkyl group" as used herein is a branched or unbranched saturated hydrocarbon group of 1 to 24 carbon atoms, such as methyl, ethyl, n propyl, isopropyl, n butyl, isobutyl, t butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "aralkyl" as used herein is an aryl group having an alkyl, alkynyl, or alkenyl group as defined above attached to the aromatic group. An example of an aralkyl group is a benzyl group.

The term "carbonate group" as used herein is represented by the formula OC(O)OR, where R can be hydrogen, an alkyl, alkenyl, alkynyl, aryl, aralkyl, cycloalkyl, halogenated alkyl, or heterocycloalkyl group described above.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-dihydroxyphenyl radical in a particular compound has the structure:

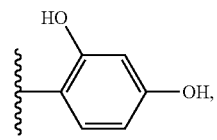

regardless of whether 2,4-dihydroxyphenyl is used to prepare the compound. In some aspects the radical (for example an alkyl) can be further modified (i.e., substituted alkyl) by having bonded thereto one or more "substituent radicals." The number of atoms in a given radical is not critical to the present disclosure unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some aspects, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

As used herein, the terms "number average molecular weight" or "$M_n$" can be used interchangeably, and refer to the statistical average molecular weight of all the polymer chains in the sample and is defined by the formula:

$$M_n = \frac{\sum N_i M_i}{\sum N_i},$$

where $M_i$ is the molecular weight of a chain and $N_i$ is the number of chains of that molecular weight. $M_n$ can be determined for polymers, e.g., polycarbonate polymers, by methods well known to a person having ordinary skill in the art using molecular weight standards, e.g. polycarbonate standards or polystyrene standards, preferably certified or traceable molecular weight standards.

$$M_n = \frac{\sum N_i M_i}{\sum N_i},$$

As used herein, the terms "weight average molecular weight" or "Mw" can be used interchangeably, and are defined by the formula:

$$M_w = \frac{\sum N_i M_i^2}{\sum N_i M_i},$$

where $M_i$ is the molecular weight of a chain and $N_i$ is the number of chains of that molecular weight. Compared to $M_n$, $M_w$ takes into account the molecular weight of a given chain in determining contributions to the molecular weight average. Thus, the greater the molecular weight of a given chain, the more the chain contributes to the $M_w$. $M_w$ can be determined for polymers, e.g. polycarbonate polymers, by methods well known to a person having ordinary skill in the art using molecular weight standards, e.g. polycarbonate standards or polystyrene standards, preferably certified or traceable molecular weight standards.

As used herein, the terms "polydispersity index" or "PDI" can be used interchangeably, and are defined by the formula:

PDI=$M_n/M_w$.

The PDI has a value equal to or greater than 1, but as the polymer chains approach uniform chain length, the PDI approaches unity.

As used herein, "polycarbonate" refers to an oligomer or polymer comprising residues of one or more dihydroxy compounds, e.g., dihydroxy aromatic compounds, joined by carbonate linkages; it also encompasses homopolycarbonates, copolycarbonates, and (co)polyester carbonates.

The terms "residues" and "structural units", used in reference to the constituents of the polymers, are synonymous throughout the specification.

As used herein the terms "weight percent," "wt %," and "wt. %," which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

Each of the materials disclosed herein are either commercially available and/or the methods for the production thereof are known to those of skill in the art.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Pida Monomer

In accordance with the purpose(s) of the disclosure, as embodied and broadly described herein, the disclosure, in one aspect, relates to monomers useful in producing alternative monomers and polymers, methods of making same, thermoplastic compositions comprising same, and articles comprising same.

In various aspects, the present disclosure relates to methods for preparing a phenylindane dicarboxylic acid (PIDA) monomer. In further aspects, the PIDA monomer has a structure represented by the formula:

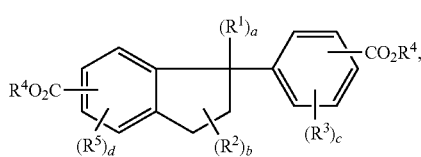

wherein $R^1$, $R^2$, $R^3$, and $R^5$ are each independently a $C_{1-3}$ alkyl group, a is 0-1, b is 0-4, c is 0-4 and d is 0-3, and each $R^4$ is independently a hydrogen or a $C_{1-3}$ alkyl group.

In various aspects, this general class of monomers are known as the dicarboxylic acid derivatives of phenylindane. In further aspects, a non-limiting list of these dicarboxylic acids include: 3-(4-carboxyphenyl)-1,1,3-trimethyl-5-indan carboxylic acid; 3-(4-carboxyphenyl)-1,3-diethyl-1-methyl-5-indan carboxylic acid; 3-(4-carboxyphenyl)-1,3-dipropyl-1-methyl-5-indan carboxylic acid, and the like.

In some aspects, the phenylindane dicarboxylic acid monomer has a structure represented by the formula:

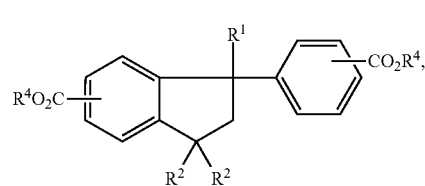

wherein each $R^4$ is independently hydrogen or a $C_{1-3}$ alkyl group.

In other aspects, the phenylindane dicarboxylic acid monomer has a structure represent by the formula:

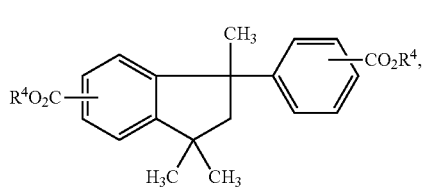

wherein wherein each $R^4$ is independently hydrogen or a $C_{1-3}$ alkyl group. In still further aspects, each $R^4$ is the same and is a methyl or ethyl group. In one aspect, each $R^4$ is the same and is a methyl methyl group. In a further aspect, this monomer is known as 1,3,3-trimethyl-1-phenylindan-4',5-dicarboxylic acid; 1,1,3-trimethyl-5-carboxy-3-(p-carboxy-phenyl)indane; 1,1,3-trimethyl-5-carboxy-3-(4-carboxyphenyl)indan; and 3-(4-carboxyphenyl)-1,1,3-trimethyl-5-indan carboxylic acid. In other aspects, monomers of formula III are generally referred to as phenylindane dicarboxylic acid, or, abbreviated, PIDA.

In some aspects, the disclosed monomer is a bio-based material. In further aspects, the monomer is derived from a biological material. In some aspects, the monomer is wholly derived from a biological material. In other aspects, the monomer is partly derived from a biological material. In further aspects, the monomor not derived from organic material that has been transformed by geological processes into petroleum, petrochemicals, and combinations thereof. In further aspects, the monomer is derived from a waste product.

C. Methods of Making the Compounds and Compositions

In one aspect, the disclosure relates to methods of making a PIDA monomer useful in making polymer compositions.

In one aspect, the disclosed PIDA compounds comprise the reaction products of the synthetic methods described herein. In a further aspect, the disclosed PIDA compounds comprise a compound produced by a synthetic method described herein. In a still further aspect, the disclosure comprises a polymeric composition comprising the reaction product of the disclosed methods and one additional monomer.

In a further aspect, the PIDA compounds according to the disclosure can generally be prepared by a succession of reaction steps. In a still further aspect, the PIDA compounds can be prepared according to the following synthesis methods. The disclosed compounds may be synthesized in the form of racemic mixtures of enantiomers which can be separated from one another following separation or resolution procedures. The racemic compounds of disclosed compounds may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of disclosed compounds involves liquid chromatography using a chiral stationary phase. Said pure stereochemically isomeric forms may also be derived from the corresponding pure stereochemically isomeric forms of the appropriate starting materials, provided that the reaction occurs stereospecifically.

In various aspects, the present disclosure relates methods for preparing a phenylindane dicarboxylic acid (PIDA) monomer, the method comprising: a) reacting an alkylstyrene under reaction conditions effective to provide a reaction product comprising at least one phenylindane; and b) reacting the reaction product under reaction conditions effective to provide a reaction product comprising at least one phenylindane dicarboxylic acid (PIDA) monomer.

In one aspect, the disclosure provides a method for preparing a phenylindane dicarboxylic acid (PIDA) monomer, the method comprising: a) reacting an alkylstyrene under first reaction conditions effective to provide a first reaction product comprising at least one phenylindane; and b) reacting the first reaction product under second reaction conditions effective to provide a second reaction product comprising at least one phenylindane dicarboxylic acid (PIDA) monomer.

In one aspect, the the alkylstyrene has a structure represented by the formula:

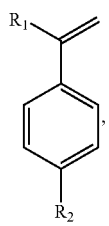

wherein each of R1 and R2 is each independently selected from hydrogen, and C1-C3 alkyl. In some aspects, the alkylstyrene is alpha-methylstyrene (AMS). In other aspect, the alkylstyrene is α-p-dimethylstyrene. In a further aspect, the alkylstyrene is provided as a waste material.

In further aspects, the phenylindane comprises reaction of alkyl styrene dimerization followed by oxidation
In some aspects, the phenylindane is trimethyl phenylindane. In other aspects, the phenylindane is tetramethyl phenylindane.

In one aspect, the phenylindane dicarboxylic acid produced by the present methods has a structure represented by the formula:

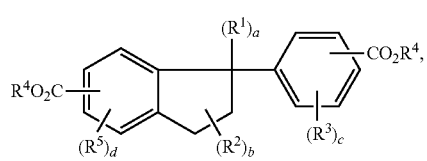

wherein $R^1$, $R^2$, $R^3$, and $R^5$ are each independently a $C_{1-3}$ alkyl group, a is 0-1, b is 0-4, c is 0-4 and d is 0-3, and each $R^4$ is independently a hydrogen or a $C_{1-3}$ alkyl group.

In further aspects, the phenylindane dicarboxylic acid can include: 3-(4-carboxyphenyl)-1,1,3-trimethyl-5-indan carboxylic acid; 3-(4-carboxyphenyl)-1,3-diethyl-1-methyl-5-indan carboxylic acid; 3-(4-carboxyphenyl)-1,3-dipropyl-1-methyl-5-indan carboxylic acid, and the like.

In some aspects, the phenylindane dicarboxylic acid monomer has a structure represented by the formula:

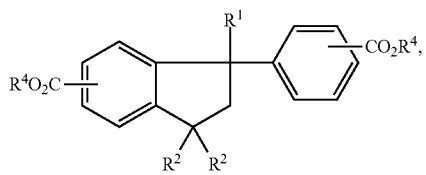

wherein each $R^4$ is independently hydrogen or a $C_{1-3}$ alkyl group.

In other aspects, the phenylindane dicarboxylic acid monomer has a structure represent by the formula:

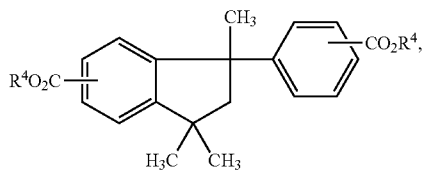

wherein wherein each $R^4$ is independently hydrogen or a $C_{1-3}$ alkyl group. In still further aspects, each $R^4$ is the same and is a methyl or ethyl group. In one aspect, each $R^4$ is the same and is a methyl methyl group. In a further aspect, the phenylindane dicarboxylic acid monomer is 1,3,3-trimethyl-1-phenylindan-4',5-dicarboxylic acid; 1,1,3-trimethyl-5-carboxy-3-(p-carboxy-phenyl)indane; 1,1,3-trimethyl-5-carboxy-3-(4-carboxyphenyl)indan; or 3-(4-carboxyphenyl)-1,1,3-trimethyl-5-indan carboxylic acid. In a further aspect, the phenylindane dicarboxylic acid is the dicarboxylic acid derivative of the phenylindane produced by the present methods. In some aspects, the phenylindane dicarboxylic acid is 1,3,3-trimethyl-1-phenylindan-4',5-dicarboxylic acid.

In various further aspects, the methods will further comprise at least one additional step. For example, according to aspects of the disclosure, the method comprises the step of reacting an alkylbenzene to provide the alkylstyrene. In further aspects, the alkylbenzene comprises. In some aspects, the alkylbenzene is p-cymene, p-bromo toluene, 4-methylacetophenone, 8-hydroxy-p-cymene, or halogenated para cymenes.

In further aspects, the method comprises the step of reacting an acetophenone to provide the alkylstyrene. In still further aspects, the method comprises the step of reacting limonene to provide the the alkylstyrene. In yet further aspects, the method comprises the step of reacting a reaction product under reaction conditions effective to provide a reaction product comprising at least one acetylated phenylindane. In still further aspects, the method comprises the step of reacting a phenylindane to provide a reaction product comprising at least one acetylated phenylindane. In even further aspects, the method comprises the step of separation of a racemic mixture.

As briefly described, the methods comprise at least one reaction or reacting step. In further aspects, reacting or the reaction step comprises any reaction condition effective to produce a desired reaction product or result, for example, reacting a reactant under reaction conditions effective to provide a reaction product comprising at least one desired compound. In still further aspects, the method can comprise any number of reaction conditions, for example, a first, second, third, fourth, and fifth reaction condition, or any combination thereof. In yet further aspects, each reacting step or reaction can comprise any number of reaction conditions, for example, a first, second, third, fourth, and fifth reaction condition, or any combination thereof. In further aspects, the method can provide any number of reaction products, for example, a first, second, third, fourth, and fifth reaction product, or any combination thereof. In still further aspects, each reacting step or reaction can provide any number of reaction products, for example, a first, second, third, fourth, and fifth reaction product, or any combination thereof.

According further aspects of the present disclosure, the method comprises the step of reacting an alkylstyrene under reaction conditions effective to provide a reaction product comprising at least one phenylindane. In a further aspect, the step is reacting an alkylstyrene under first reaction conditions effective to provide a first reaction product comprising at least one phenylindane.

In various aspects, the reaction conditions comprise reacting at least one reactant in the presence of a catalyst. In further aspects, the reaction conditions comprise reacting the alkylstyrene in the presence of a catalyst. In still further aspects, the catalyst is a dimerization catalyst, or a acid catalyst In yet further aspects, the catalyst comprises comprises an acid catalyst, ion exchange resin catalyst, iluoric acids, hydroiodic acid, hydrobromic acid, or solid acid catalysts, In some aspects, the catalyst comprises hydrochloric acid, sulfuric acid or nitric acid, amberlyst-15, Nafion, K-2661, or Lewasorb AC 10FT In further aspects, non-limiting acid catalysts include mineral acids such as sulfuric, nitric, phosphoric, and hydrochloric acids and solid acid catalysts, such as sulfonated styrene/divinylbenzene polymer beads and zeolites, Fulcat, Al2O3-TiO2, TiO2-ZrO2, SiO2-Al2O3 or acidic clays, hetero poly acids, silico-tungstic acids, Lewis acids In still further aspects, the catalyst can comprise $H_2SO_4$, an ion exchange resin catalyst, an cationic acidic ion exchange resin, a sulfonated polystyrene resin catalyst cross linked with divinyl benzene, trifluoro acetic acid, toluene sulfonic acid, trifluromethane sulfonic acid, dodecyl benzene sulfonic acid (DBSA), HCl, or a combination thereof. In some aspects, the catalyst is $H_2SO_4$, an ion exchange resin catalyst, C1-C24 alkyl or alkyl aryl sulfonic acid, HCl, or a combination thereof. In other aspects, the catalyst is HCl.

In further aspects, conditions effective can comprise adjusting the temperature to at least about 50° C. In still further aspects, the temperature is adjusted to a temperature of from 0° C. to about 250° C., including exemplary temperatures of about 55, 60, 65, 70, 75, 80, 85, 90, 95, 100, 105, 110, 115, 120, 125, 130, 135, 140, 145, 155, 160, 165, 170, 175, 180, 185, 190, 195, 200, 205, 210, 215, 220, 225, 230, 235, 240, and 245° C.

In further aspects, conditions effective can comprise maintaining the reaction for at least about 1 hour. In still further aspects, the reaction is maintained for about 1 to about 20 hours, including exemplary times of 2, 3, 4, 5, 6, 7, 8, 9, 10, 11, 12, 13, 14, 15, 16, 17, 18, and 19 hours.

In further aspects, conditions effective can comprise adjusting the pH to a range of from 1 to about 6, including exemplary values of 2, 3, 4, 5, and 6.

In further aspects, the reaction conditions can comprise oxidative reaction conditions. In still further aspects, the reaction conditions comprise reacting a reactant in the presence of an oxidizing agent. In even further aspects, the reaction conditions comprise reacting a reaction product comprising at least one phenylindane in the presence of an oxidizing agent to provide a phenylindane dicarboxylic acid monomer. In yet further aspects, the reaction conditions comprise reacting a reaction product in the presence of an oxidizing agent, for example, reacting a reaction product in the presence of $KMnO_4$ and pyridine.

In further aspects, the oxidizing agent can comprise $KMnO_4$, pyridine, ceric ammonium nitrate, nitric acid, Chromium trioxide or mixture of Concentrated H2SO4-Chromic Anhydride. Chromic anhydride(CrO3), oxygen containing heavy metals such as manganese, cobalt, lead, iron, nickel, copper, vanadium can also be used. Also, oxides, hydroxides or organic salts of any of such metals or their combinations can be used.

In further aspects, reacting or the reaction step is acetylating or haloacetylating with an acetylating agent in the presence of a Friedel-Crafts catalyst to provide a reaction product comprising an isomer mixture. In still further aspects, reacting or the reaction step is reacting a phenylindane with an acetyl halide to provide a reaction product comprising at least one acetylated phenylindane.

In further aspects, the acetylating agent comprises acetyl chloride, chloroacetyl chloride or acetic anhydride, or a combination thereof. In still further aspects, the Friedel-Crafts catalyst comprises aluminum chloride, zinc chloride, or iron (III) chloride, or a combination thereof.

Other Friedel-Crafts catalyst that can be included are Zeolite (aluminosilicate), Mordenite, Nafion H, Lithium salts, Indium salts, Lewis acids.

In further aspects, reacting or the reaction step comprises brominating an alkylbenzene to provide a reaction product comprising a mixture of mono- and di-brominated alkylbenzene products. In still further aspects, reacting or the reaction step is reacting an alkylbenzene in the presence of $KBrO_3$ and $NaHSO_3$ to provide a reaction product comprising a mixture of mono- and di-brominated alkylbenzene products. In yet further aspects, reacting or the reaction step is reacting p-cymene in the presence of $KBrO_3$ and $NaHSO_3$ to provide a reaction product comprising a mixture of mono-brominated p-cymene and di-brominated p-cymene products.

In further aspects, reacting or the reaction step comprises reacting a brominated alkylbenzene to provide a reaction product comprising an alkylstyrene. In still further aspects, reacting or the reaction step is dehydrohalogenating a brominated alkylbenzene to provide a reaction product comprising a alkylstyrene. In further aspects, reacting or the reaction step is reacting a brominated alkylbenzene in the presence of aliphatic hydrocarbons to provide a reaction product comprising an alkylstyrene. In yet further aspects, reacting or the reaction step is reacting a brominated alkylbenzene in the presence of n-heptane to provide a reaction product comprising an alkylstyrene, for example, reacting 8-bromo-p-cymene to provide the corresponding α-p-dimethyl styrene.

In further aspects, reacting or the reaction step can comprise Gringard reaction conditions effective to provide a reaction product comprising a Gringard reagent. In still further aspects, reacting or the reaction step comprises reacting an alkylbenzene with magnesium to provide a reaction product comprising a Gringard reagent, for example, reacting p-bromo toluene with magnesium turnings to provide the Grignard reagent p-methyl phenyl magnesium bromide. In yet further aspects, reacting or the reaction step comprises reacting an acetophenone using Grignard reagent to provide a reaction product comprising alkylstyrene. In even further aspects, reacting or the reaction step comprises reacting acetophenone in the presence of methyl magnesium bromide to provide a reaction product comprising α-p-dimethyl styrene.

In various aspects, the method can further comprise purification of the reaction product. In further aspects, the reaction product is subjected to at least one purification step. In still further aspects, the purification comprises dissolving the reaction product using aqueous NaOH solution. In still further aspects, the purification comprises dissolving the reaction product using aqueous alkali solution. In still further aspects, the purification comprises dissolving the reaction product using aqueous NaHCO3 solution. In yet further aspects, the reaction product is dissolved at room temperature. In yet further aspects, the reaction product is dissolved at 100° C. and then cooled. In even further aspects, the pH of the reaction product is adjusted to pH effective to provide a solid reaction product. In still further aspects, the pH is adjusted to less than about 3.

In further aspects, the reaction product is purified under conditions effective to provide purified reaction product comprising at least 50 wt % PIDA. In still further aspects, the purified reaction product comprises from about 50 to about 100 wt % PIDA, including exemplary values of 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and 99 wt %.

In further aspects, the purification can further comprise the step of filtering, separating, washing, or drying, or a combination thereof. In still further aspects, purification can comprise dissolving in glacial acetic acid. In yet further aspects, the filtering can be performed over celite bed, charcoal bed or silica or neutral alumina bed.

In various aspects, the method can further comprise separation of the reaction product. In further aspects, the reaction product is subjected to at least one separation step.

In still further aspects, separation comprises chiral separation of a racemic mixture using flash chromatography. In yet further aspects, high pressure liquid chromatography (HPLC) can be used. In still further aspects, the HPLC column can comprise commercially available enantioselective stationary phase: cellulose tris(3,5-dimethylphenylcarbamate) immobilized on silica-gel, cellulose tris(4-methylbenzoate) immobilized on silica-gel, or amylose tris(3,5-dimethylphenylcarbamate) immobilized on silica-gel or other amylose-based or cellulose based columns as available. In even further aspects, the HPLC column can be or comprise one or more commercial available columns such as Daicel CHIRALPAK® IA, IC, ID or IF, Phenomenex Lux® Amylose-2, Lux® Cellulose-1, Supelco Astec® Cellulose DMP, or a combination thereof. In some aspects, the HPLC column is a CHIRALPAK IC. In other aspects, the HPLC column is a CHIRALPAK IA column.

In various aspects, the methods can provide improved yield and selectivity of the desired reaction product. In further aspects, the method can provide a product yield of at least about 60% to about 80% with about 90-95% selectivity towards PIDA compared to traditional PIDA process.

Based on the method which used for PIDA synthesis, yield ranges from about 30 to about 90% and selectivity ranges from about 20 to about 95% and purity ranges from about 40% to about 99.5%.

In further aspects, advantages of these PIDA synthesis routes are traditional synthesis methods of PIDA, give low yields of product and require rigorous reaction conditions, such as, the use of propylene gas, high pressure and high temperature. In a further aspect, the prior methods lack chemo-selectivity, and thus, restrict the scale-up production of PIDA in large quantities. Present methods are more robust, give high yield and selectivity, requires less rigorous reaction conditions In further aspects, the PIDA monomer of the reaction product is an ortho alkoxy bisphenol monomer.

In further aspects, the reaction product comprises at least about 10 wt % of the PIDA monomer. In still further aspects, the reaction product comprises from at least about 1 wt % to about 100 wt % of PIDA monomer, including exemplary wt % of 5, 10, 15, 20, 25, 30, 35, 40, 45, 50, 55, 60, 65, 70, 75, 80, 85, 90, and 95 wt %. In yet further aspects, the reaction product comprises at least about 10 wt % of PIDA. In even further aspects, the reaction product comprises from at least about 10 wt % to about 100 wt % of PIDA, including exemplary wt % of 20, 25, 30, 35, 40, 45, 50, 55, 60, 65, 70, 75, 80, 85, 90, and 95 wt %. In still further aspects, the reaction product comprises at least about 10 wt % of the PIDA. In yet further aspects, the reaction product comprises from at least about 10 wt % to about 100 wt % of PIDA, including exemplary wt % of 20, 25, 30, 35, 40, 45, 50, 55, 60, 65, 70, 75, 80, 85, 90, and 95 wt %.

The compounds of this disclosure can be prepared by the disclosed methods employing reactions as shown in the disclosed schemes, in addition to other standard manipulations that are known in the literature, exemplified in the experimental sections or clear to one skilled in the art. The following examples are provided so that the disclosure might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the disclosure. It is understood that a disclosed method can be used to provide the disclosed compounds. It is also understood that the products of the disclosed methods can be employed in the disclosed compositions, methods, and uses.

1. Synthesis Route 1

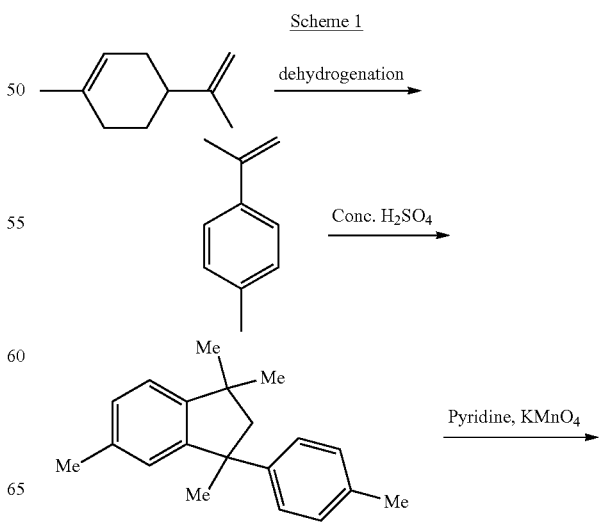

Scheme 1

-continued

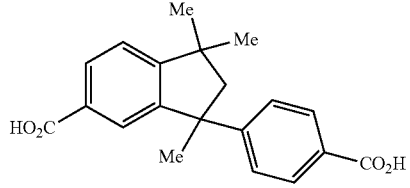

In one aspect, a terpene, terpenoid, or combination thereof, such as limonene, is dehydrogenated with a catalyst at a temperature effective and for a time effective to produce α-p-dimethylstyrene, which in turn can be readily cyclized and oxidized at a temperature effective and for a time effective to give the corresponding PIDA. The scheme should be modified to show that traditional Paraxylene oxidation to PTA process, in addition to Pyridine, KMnO4 can also be employed to convert dimethyl adduct to PIDA.

2. Synthesis Route 2

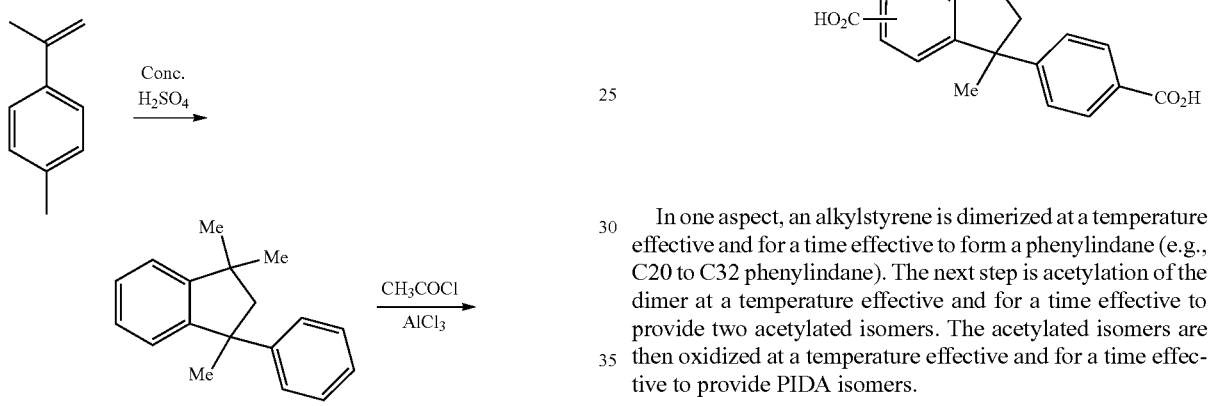

-continued

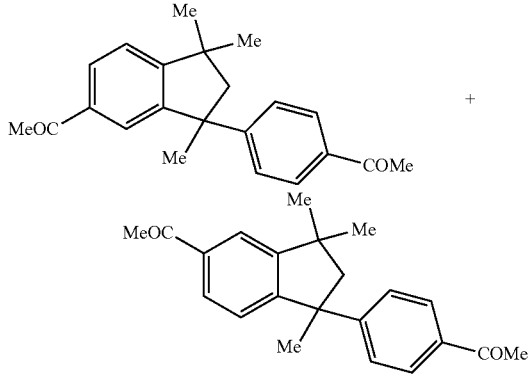

In one aspect, an alkylstyrene is dimerized at a temperature effective and for a time effective to form a phenylindane (e.g., C20 to C32 phenylindane). The next step is acetylation of the dimer at a temperature effective and for a time effective to provide two acetylated isomers. The acetylated isomers are then oxidized at a temperature effective and for a time effective to provide PIDA isomers.

3. Synthesis Route 3

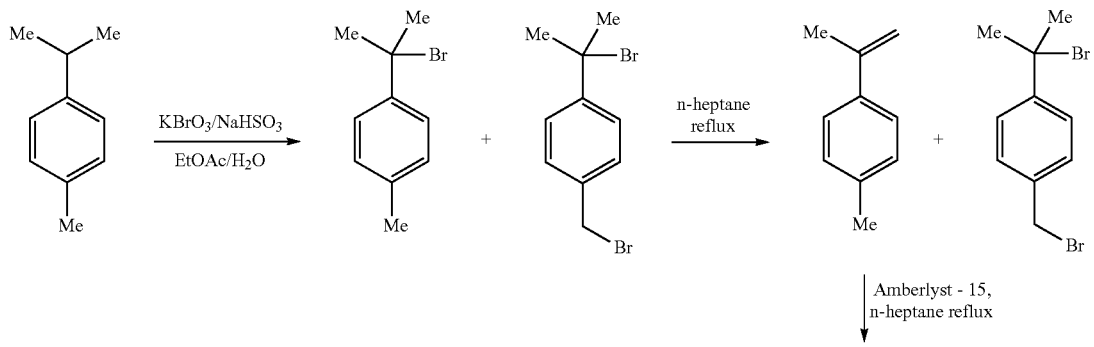

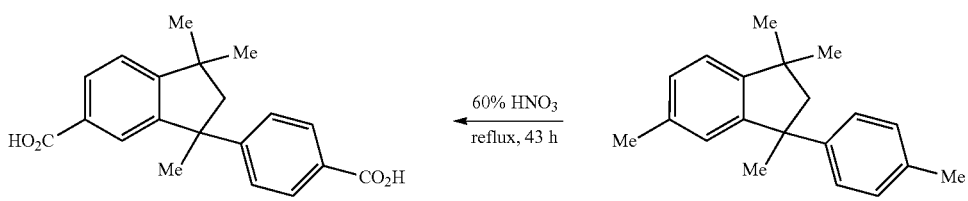

In one aspect, alkylbenzene is brominated at a temperature effective and for a time effective to produce a mixture of brominated alkylbenzene products, followed by selective dehydrohalogenation at a temperature effective and for a time effective to give the corresponding alkylstyrene along with unreacted brominated alkylbenzene. The alkylstyrene mixture can then undergo cyclization at a temperature effective and for a time effective to give the corresponding cyclized dimer, and then oxidized at a temperature effective and for a time effective to produce PIDA.

4. Synthesis Route 4

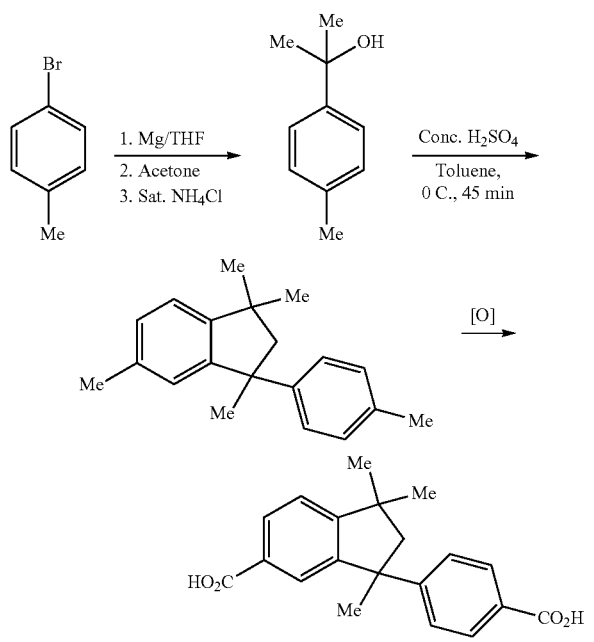

In one aspect, brominated alkylbenzene is reacted with magnesium turnings in dry THF as solvent, followed with treatment with the solution of acetone in dry THF, and subsequent quenching of Grignard reaction using saturated NH$_4$Cl solution at temperatures effective and for times effective to result in the formation of a further alkylbenzene. Dimerization of alkylbenzene at a temperature effective and for a time effective gives the corresponding dimer.

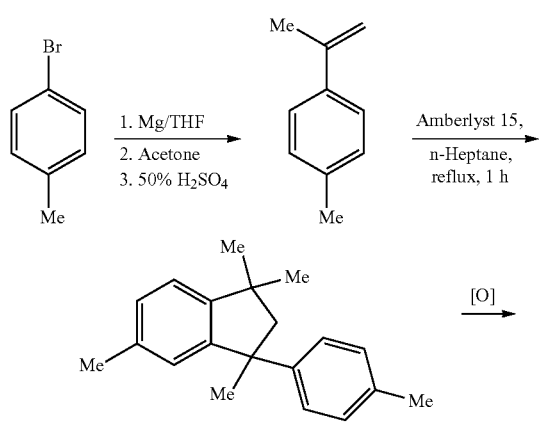

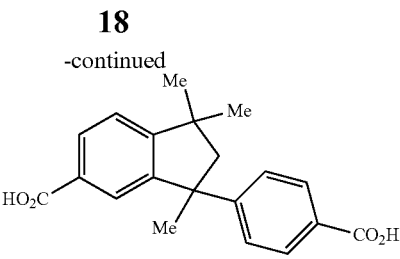

Alternatively, quenching of the Grignard reaction using concentrated H$_2$SO$_4$ solution at a temperature effective and for a time effective affords the corresponding alkylstyrene. Dimerization of alkylstyrene at a temperature effective and for a time effective gives the corresponding dimer. Finally, oxidation of the dimer at a temperature effective and for a time effective gives PIDA.

5. Synthesis Route 5

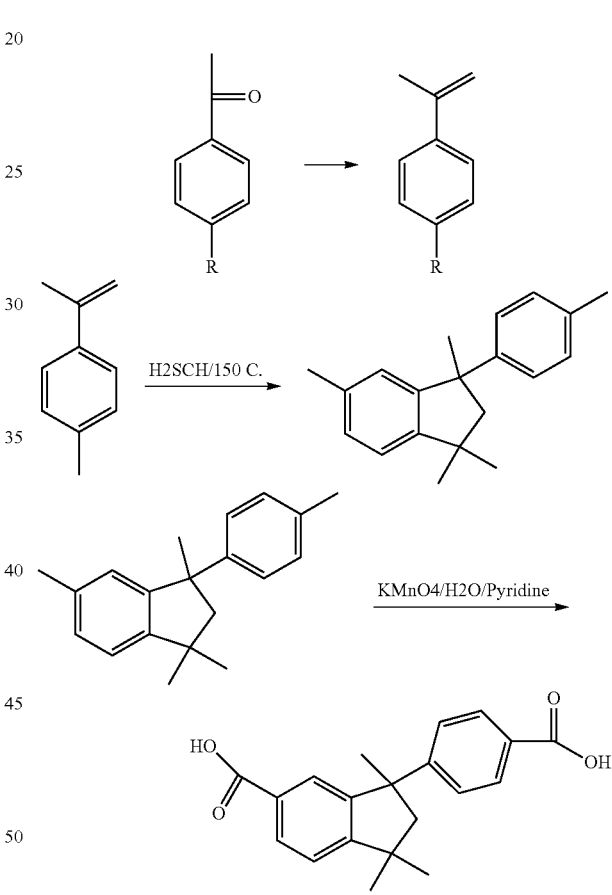

In one aspect, an alkylstyrene is synthesized from an acetophenone derivative using Grignard reagent, followed by dimerization of alkylstyrene in acidic media at a temperature effective and for a time effective to provide the corresponding dimer. Finally, the dimer molecule is selectively oxidized using potassium permanganate (KMn04) in pyridine water system at a temperature effective and for a time effective to provide PIDA.

In an aspect, intermediates and the product formation were confirmed by LCMS & NMR, purity by GC & HPLC.

In various aspects, the disclosed PIDA monomers are useful for making polymers and polymer compositions. In one aspect, the present disclosure provides polyester compositions. In further aspects, the polyester composition comprises a polyester. In still further aspects, the polyester composition comprises a copolyester.

In general, polyesters, as described herein, are produced by polymerization of at least one dicarboxylic acid or reactive derivative thereof and a diol or reactive derivative thereof, and have repeating units of formula (A):

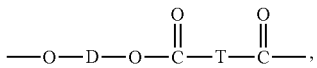

wherein T is a residue derived from a dicarboxylic acid or chemical equivalents thereof, and D is a residue derived from a diol or chemical equivalents thereof. As used herein, chemical or reactive equivalents of diacids include dialkyl esters, e.g., dimethyl esters, diaryl esters, anhydrides, salts, acid chlorides, acid bromides, and the like. As used herein, chemical or reactive equivalents of diols include esters, such as dialkylesters, diaryl esters, and the like.

In addition to units comprising a dicarboxylic acid or chemical equivalent thereof, and a diol or chemical equivalent thereof, other T and/or D units can be present in the polyester, provided that the type or amount of such units do not significantly adversely affect the desired properties of the polymer compositions.

In various aspects, the polyester compositions of the present disclosure are produced by polymerization of a dicarboxylic acid, or reactive derivative thereof, and a diol or reactive derivative thereof. In a further aspect, the polyester compositions are produced by polymerization of a dicarboxylic acid component derived from a phenylindane dicarboxylic acid (PIDA) or reactive thereof; and a diol component.

Other Monomers:

In aspects, polyesters can be obtained by interfacial polymerization or melt-process condensation, by solution phase condensation, or by transesterification polymerization using acid catalysis. The catalyst facilitates the transesterification reaction, and can comprise cerium compounds, zinc compounds, antimony compounds, tin compounds, titanium compounds, germanium compounds, zirconium compounds, and combinations thereof, as well as many other metal catalysts and combinations of metal catalysts that have been disclosed in the literature. The amount of catalyst required to obtain an acceptable polymerization rate at the desired polymerization temperature will vary, and can be determined by experimentation. In some aspects, the catalyst amount can be 1 to 5000 ppm, or more. In further aspects, the catalyst amount can be 50 to 300 ppm. In one aspect, when an alkyl ester of the dicarboxylic acid compound is employed, an ester interchange type of catalyst is preferred, such as $Ti(OC_4H_9)_6$ in n-butanol.

For example, in one aspect, the present disclosure provides a method for preparing a polyester composition, the method comprising: a) providing a dicarboxylic acid component comprising at least one PIDA monomer; b) providing a diol combonent; and d) reacting the dicarboxylic acid component and diol component under conditions effective to provide a reaction product comprising a polyester.

In another aspect, the present disclosure provides a method for preparing a polyester composition, the method comprising: a) providing a dicarboxylic acid component comprising at least one PIDA monomer; b) providing a terephthalate component comprising at least one di(C1-3 alkyl) terephthalate, or terephthalic acid, or a combination thereof; c) a diol combonent; and d) reacting the dicarboxylic acid component, terephthalate component, and diol component under conditions effective to provide a reaction product comprising a polyester.

In one aspect, it is possible to prepare branched polyester in which a branching agent, for example, a glycol having three or more hydroxyl groups or a trifunctional or multifunctional carboxylic acid has been incorporated. In a further aspect, it is sometimes desirable to have various concentrations of acid and hydroxyl end groups on the polyester, depending on the ultimate end use of the composition.

In various aspects, the polyester compositions of the present disclosure have an intrinsic viscosity of at least 0.7 deciliters per gram (dL/g), as measured in phenol/tetrachloroethane (60:40, volume/volume ratio) at 25° C. In a further aspect, the polyester composition has an intrinsic viscosity (as measured in phenol/tetrachloroethane (60:40, volume/volume ratio) at 25° C.) ranging from at least about 0.7 to about 2.0 deciliters per gram. In a yet further aspect, the polyester composition has an intrinsic viscosity (as measured in chloroform at 25° C.) ranging from at least about 0.7 to about 1.2 deciliters per gram. In a still further aspect, the polyester composition has an intrinsic viscosity (as measured in chloroform at 25° C.) ranging from at least about 0.8 to about 1.0 deciliters per gram.

In a further aspect, the polyester composition has a weight average molecular weight from about 5,000 to about 130,000 g/mol as determined by gel permeation chromatography in chloroform/hexafluoroisopropanol (5:95, volume/volume ratio) at 25° C. using polystyrene standards. In a still further aspect, the polyester has a weight average molecular weight from about 10,000 to about 200,000 g/mol as determined by gel permeation chromatography in chloroform/hexafluoroisopropanol (5:95, volume/volume ratio) at 25° C. using polystyrene standards. In a yet further aspect, the polyester composition has a weight average molecular weight from about 30,000 to about 200,000 g/mol as determined by gel permeation chromatography in chloroform/hexafluoroisopropanol (5:95, volume/volume ratio) at 25° C. using polystyrene standards. In an even further aspect, the polyester composition has a weight average molecular weight from about 50,000 to about 200,000 g/mol as determined by gel permeation chromatography in chloroform/hexafluoroisopropanol (5:95, volume/volume ratio) at 25° C. using polystyrene standards. In a still further aspect, the polyester composition has a weight average molecular weight from about 60,000 to about 200,000 g/mol as determined by gel permeation chromatography in chloroform/hexafluoroisopropanol (5:95, volume/volume ratio) at 25° C. using polystyrene standards.

In a further aspect, the polyester composition has a Tg ranging from about 107 to about 140, including exemplary Tg of 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, and 139° C.

In a further aspect, the polyester compositions are substantially transparent. In a further aspect, the polyester compositions can exhibit a level of transmittance that is greater than 50%, including exemplary transmittance values of at least 60%, 70%, 80%, 85%, 90%, and 95%, or any range of transmittance values derived from the above exemplified values. In a still further aspect, the polyester compositions exhibit relatively high levels of transparency characterized by exhibiting a transmittance of at least 80%. In a yet further aspect, the transparency can be measured for a disclosed polymer composition according to ASTM method D1003.

In a further aspect, the polyester compositions have a carboxylic end group content of less than about 100 mEq/kg, including values of less than about 90, 80, 70, 60, 50, 60, 50, 30, 20, and 10 mEq/kg. In a still further aspect, the polyester compositions have a carboxylic end group content of greater than 0 to about 100 mEq/kg, for example, from about 10 to about about 100 mEq/kg.

In a further aspect, the polyester compositions preferably exhibit a level of "haze" that is less than 80%, including haze values of less than 70%, 60%, 50%, 40%, 30%, 20%, 10%, 5%, and 1%, or any range derived from these values. In a still further aspect, the polyester compositions exhibit relatively low levels of haze characterized by exhibiting a "haze" value that is less than 20%. In a yet further aspect, haze can be measured for a disclosed polymer composition according to ASTM method D1003.

In a further aspect, the polyester composition is an amorphous copolyester. In a still further aspect, the polyester composition does not exhibit a crystalline melting point as determined by differential scanning calorimetry (DSC). In a yet further aspect, the polyester composition does not exhibit a crystalline melting point having an enthalpy of less than about 1 J/gm.

In various aspects, the present disclosure also relates to thermoplastic compositions comprising the disclosed polyester compositions. In further aspects, polyester compositions of the present disclosure are useful as a component in thermoplastic compositions.

According to aspects of the disclosure, the thermoplastic composition is a polymer blend. In a further aspect, the polymer blend comprises a) a first polymer component comprising at least one polyester composition described in the present disclosure; and b) a second polymer component. In a still further aspect, the second polymer component comprises one or more of at least one polycarbonate, polyester, styrene acrylonitrile, acrylonitrile butadiene styrene, methyl methacrylate, methacrylate butadiene styrene, styrene maleic anhydride, styrene butadiene styrene, styrene ethylene butadiene styrene, polystyrene, polyolefin, polyetherimide, or a combination thereof.

In one aspect, the polyester composition can be present in the thermoplastic composition in an amount from 20 to 99.99 wt. %, or from 20 to 95 wt. %, or from 30 to 80 wt. %, based on the total weight of the composition, including exemplary wt. % of at least 50 wt. %, at least 60 wt. %, at least 70 wt. %, of the copolyester can be present. In a further aspect, the polyester composition is present in an amount from 50 to 99 wt. %, based on the total weight of the thermoplastic composition, including exemplary wt. % ranges of from 60 to 98 wt. %, and 70 to 95 wt. %, each amount based on the total weight of the thermoplastic composition. The remaining components of the thermoplastic compositions can be other additives, including other polymers, as described below.

In a further aspect, the thermoplastic composition can optionally comprise other polyesters and/or other polymers, for example, other polyesters or polycarbonates. As used herein, "polyesters" is inclusive of homopolymers and copolymers comprising ester units, and "polycarbonate" is inclusive of homopolymers and copolymers comprising carbonate units. Exemplary polyesters include poly(ethylene terephthalate) ("PET"), poly(1,4-butylene terephthalate), ("PBT"), poly(ethylene naphthalate) ("PEN"), poly(butylene naphthalate), ("PBN"), poly(1,3-propylene terephthalate) ("PPT"), poly(cyclohexane-1,4-dimethylene terephthalate) ("PCT"), poly(cyclohexane-1,4-dimethylene cyclohexane-1,4-dicarboxylate) also known as poly(1,4-cyclohexanedimethanol 1,4-dicarboxylate) ("PCCD"), and poly(cyclohexylene-1,4-dimethylene-co-ethylene terephthalate), also known as cyclohexanedimethanol-terephthalic acid-ethylene glycol ("PCTG" or "PETG") copolymers. When the molar proportion of cyclohexanedimethanol is higher than that of ethylene glycol the polyester is termed PCTG. When the molar proportion of ethylene glycol is higher than that of cyclohexane dimethanol the polyester is termed PETG. As is known in the art, the foregoing polyesters can further comprise units comprising isophthalic acid. Combinations of the foregoing polymers can be used. The other polymer can be present in an amount of from 0.01 to 80 wt. %, or from 5 to 80 wt. %, or from 30 to 70 wt. %, each based on the total weight of the polyester and the other polymers in the thermoplastic composition. For example, in one aspect, a thermoplastic composition can comprise copolyester produced from the combination of the precursor component (a), the terephthalate component (b), and and 1,4-cyclohexane dimethanol (CHDM) (c), can comprise from 1 to 80 wt. % percent, or from 5 to 80 wt. %, or from 30 to 70 wt. %, based on the total weight of the polyesters and other polymers in the thermoplastic composition, of a second polyester, for example poly(ethylene terephthalate), poly(ethylene naphthalate), poly(1,4-butylene naphthalate), poly(trimethylene terephthalate), poly(1,4-cyclohexanedimethylene 1,4-cyclohexanedicarboxylate), poly(1,4-cyclohexanedimethylene terephthalate), poly(1,4-butylene-co-1,4-but-2-ene diol terephthalate), poly(1,4-cyclohexanedimethylene-co-ethylene terephthalate), or a combination comprising at least one of the foregoing polyesters. In other aspects, the thermoplastic composition can comprise 1 to 50 wt. %, or 1 to 30 wt. %, or 1 to 10 wt. %, based on the total weight of the polyester and other polymers in the composition, of a polycarbonate and/or an aromatic copolyester carbonate. In further aspects, the polymer component of the thermoplastic composition consists only of the copolyester. In other aspects, the polymer component comprises at least 70 wt. % of the copolyester. In some aspects, the other polymer includes one or more impact modifiers. The thermoplastic composition can thus comprise the copolyester and optionally, an impact modifier.

In further aspects, the thermoplastic composition comprises at least one additive. In one aspect, the thermoplastic composition can optionally further comprise an impact modifier in an amount from 0.25 to 40 wt. %, including exemplary ranges of from 0.5 to 25 wt. %, or from 1 to 10 wt. %, based on the total weight of the composition. In further aspects, the impact modifier is present in an amount from 0.5 to 8 wt. %, including exemplary ranges of from 1.0 to 6 wt. %, or 0 to 1.0 wt. %, based on the total weight of the composition. In some aspects, the thermoplastic composition does not include an impact modifier or does not contain appreciable amounts of an impact modifier. In other aspects, the impact modifier is present in an amount, based on wt. %, ranging from 0 to less than an integer selected from the group consisting of 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 wt. %, and combinations thereof.

Exemplary and non-limiting impact modifiers include olefin-containing copolymers such as olefin acrylates and olefin diene terpolymers. An example of an olefin acrylate copolymer impact modifier is ethylene ethylacrylate copolymer available from Union Carbide as DPD-6169. Other higher olefin monomers can be employed as copolymers with alkyl acrylates, for example, propylene and n-butyl acrylate. Olefin diene terpolymers known in the art and generally fall into the EPDM (ethylene propylene diene monomer) family of terpolymers. They are commercially available such as, for example, EPSYN® 704 from Copolymer Rubber Company. Examples of such rubber polymers and copolymers that can be used as impact modifiers are polybutadiene, polyisoprene, and various other polymers or copolymers having a rubbery dienic monomer, for example, random copolymers of styrene and butadiene (SBR).

In further aspects, other thermoplastic impact modifiers are unit copolymers, for example, A-B diblock copolymers and A-B-A triblock copolymers having of one or two alkenyl aromatic units A, which are typically styrene units, and a rubber unit, B, which is typically an isoprene or butadiene unit. The butadiene unit may be partially hydrogenated. Mixtures of these diblock and triblock copolymers are especially useful. Examples of A-B and A-B-A copolymers include polystyrene-polybutadiene, polystyrene-poly(ethylene-propylene), polystyrene-polyisoprene, poly(a-methylstyrene)-polybutadiene, polystyrene-polybutadiene-polystyrene (SBS), polystyrene-poly(ethylene-propylene)-polystyrene, polystyrene-polyisoprene-polystyrene and poly(alpha-methylstyrene)-polybutadiene-poly(alpha-methylstyrene), as well as the selectively hydrogenated versions thereof, and the like. Mixtures of the aforementioned unit copolymers are also useful. Styrene-containing polymers can also be used as impact modifiers.

In some aspects, other copolymers containing vinyl aromatic compounds, for example styrene, para-methyl styrene, or alpha methyl styrene and vinyl cyanides, for example acrylonitrile or methacrylonitrile, may also be useful as impact modifiers. One example is styrene-acrylonitrile (SAN), comprising 15 to 30 percent by weight acrylonitrile (AN) with the remainder styrene. The SAN may be further modified by grafting to a rubbery substrate such as a 1,4-polybutadiene to produce a rubber graft polymer, e.g., acrylonitrile-butadiene-styrene (ABS), and methacrylonitrile-butadiene-styrene (MBS). High rubber content (greater than about 50 wt. %) resins of this type (e.g., HRG-ABS) may be especially useful In further aspects, these types of polymers are often available as core-shell polymers. The core usually consists substantially of an acrylate rubber or a butadiene rubber, wherein one or more shells have been grafted on the core. Usually these shells are built up from a vinyl aromatic compound, a vinyl cyanide, an alkyl acrylate or methacrylate, acrylic acid, methacrylic acid, or a combination of the foregoing. The core and/or the shell(s) often comprise multi-functional compounds that may act as a cross-linking agent and/or as a grafting agent. These polymers are usually prepared in several stages. In still further aspects, other impact modifiers include various elastomeric materials such as organic silicone rubbers, elastomeric fluorohydrocarbons, elastomeric polyesters, random unit polysiloxane-polycarbonate copolymers, and the like.

Exemplary and non-limiting examples of useful impact modifiers include acrylonitrile-butadiene-styrene, methacrylate-butadiene-styrene, high impact polystyrene, and combinations thereof.

In further aspects, the thermoplastic composition, in addition to the polyester composition, can optionally comprise a balance amount of one or more additive materials ordinarily incorporated in thermoplastic resin compositions of this type, with the proviso that the additives are selected so as to not significantly adversely affect the desired properties of the composition. Combinations of additives can be used. Such additives can be mixed at a suitable time during the mixing of the components for forming the composition. Exemplary and non-limiting examples of additive materials that can be present in the disclosed compositions include additional reinforcing fillers, an acid scavenger, anti-drip agent, antioxidant, antistatic agent, chain extender, colorant (e.g., pigment and/or dye), de-molding agent, flow promoter, lubricant, mold release agent, plasticizer, quenching agent, flame retardant stabilizer (including for example a thermal stabilizer, a hydrolytic stabilizer, or a light stabilizer), UV absorbing additive, and UV reflecting additive, or any combination thereof. In a further aspect, the additive is selected from an antioxidant, antistatic agent, chain extender, colorant, de-molding agent, dye, flow promoter, flow modifier, light stabilizer, lubricant, mold release agent, pigment, quenching agent, thermal stabilizer, UV absorbent substance, UV reflectant substance, and UV stabilizer, or combinations thereof.

In a further aspect, the thermoplastic compositions can further comprise a primary antioxidant or "stabilizer" (e.g., a hindered phenol) and, optionally, a secondary antioxidant (e.g., a phosphate and/or thioester). Suitable antioxidant additives include, for example, organic phosphites such as tris (nonyl phenyl)phosphite, tris(2,4-di-t-butylphenyl)phosphite, bis(2,4-di-t-butylphenyl)pentaerythritol diphosphite, distearyl pentaerythritol diphosphite or the like; alkylated monophenols or polyphenols; alkylated reaction products of polyphenols with dienes, such as tetrakis[methylene(3,5-di-tert-butyl-4-hydroxyhydrocinnamate)]methane, or the like; butylated reaction products of para-cresol or dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds such as distearylthiopropionate, dilaurylthiopropionate, ditridecylthiodipropionate, octadecyl-3-(3,5-di-tert-butyl-4-hydroxyphenyl)propionate, pentaerythrityl-tetrakis[3-(3,5-di-tert-butyl-4-hydroxyphenyl) propionate or the like; amides of beta-(3,5-di-tert-butyl-4-hydroxyphenyl)-propionic acid or the like, or combinations comprising at least one of the foregoing antioxidants.

In a further aspect, the antioxidant is a primary antioxidant, a secondary antioxidant, or combinations thereof. In a still further aspect, the primary antioxidant is selected from a hindered phenol and secondary aryl amine, or a combination thereof. In yet a further aspect, the hindered phenol comprises one or more compounds selected from triethylene glycol bis[3-(3-t-butyl-5-methyl-4-hydroxyphenyl)propionate], 1,6-hexanediol bis[3-(3,5-di-t-butyl-4-hydroxyphenyl)propionate], 2,4-bis(n-octylthio)-6-(4-hydroxy-3,5-di-t-butylanilino)-1,3,5-triazine, pentaerythrityl tetrakis[3-(3,5-di-t-butyl-4-hydroxyphenyl)propionate], 2,2-thiodiethylene bis[3-(3,5-di-t-butyl-4-hydroxyphenyl)propionate], octadecyl 3-(3,5-di-t-butyl-4-hydroxyphenyl)propionate, N,N'-hexamethylene bis(3,5-di-t-butyl-4-hydroxy-hydrocinnamamide), tetrakis(methylene 3,5-di-tert-butyl-hydroxycinnamate) methane, and octadecyl 3,5-di-tert-butylhydroxyhydrocinnamate. In an even further aspect, the hindered phenol comprises octadecyl-3-(3,5-di-t-butyl-4-hydroxyphenyl)-propionate.

In a further aspect, the secondary anti-oxidant is selected from an organophosphate and thioester, or a combination thereof. In a still further aspect, the secondary anti-oxidant comprises one or more compounds selected from tetrakis(2, 4-di-tert-butylphenyl) [1,1-biphenyl]-4,4'-diylbisphosphonite, tris(2,4-di-tert-butylphenyl)phosphite, bis(2,4-di-tert-butylphenyl)pentaerythritol diphosphite, bis(2,4-dicumylphenyl)pentaerytritoldiphosphite, tris(nonyl phenyl) phosphite, and distearyl pentaerythritol diphosphite. In yet a further aspect, the secondary anti-oxidant comprises tris(2,4-di-tert-butylphenyl)phosphite.

Antioxidants are generally used in amounts of about 0.01 wt % to about 3 wt %, optionally about 0.05 wt % to about 2.0 wt % of the thermoplastic composition.

In a further aspect, the primary antioxidant is present in an amount from about 0.01 wt % to about 3 wt %. In another aspect, the primary antioxidant is present in an amount from about 0.01 wt % to about 2.5 wt %. In still another aspect, the primary antioxidant is present in an amount from about 0.5 wt % to about 2.5 wt %. In yet a further aspect, the primary antioxidant is present in an amount from about 0.5 wt % to about 2.0 wt %. In still another aspect, the primary antioxidant is present in an amount from about 0.1 wt % to about 0.5 wt %. In still another aspect, the primary antioxidant is present in an amount from about 0.2 wt % to about 0.5 wt %. In still another aspect, the primary antioxidant is present in an amount from about 0.2 wt % to about 0.4 wt %. In a yet further aspect, the primary anti-oxidant is present in an amount from about 0.01 wt % to about 0.50 wt %. In an even further aspect, the primary anti-oxidant is present in an amount from about 0.05 wt % to about 0.25 wt %.

In a further aspect, the secondary antioxidant is present in an amount from about 0.01 wt % to about 3.0 wt %. In another aspect, the secondary antioxidant is present in an amount from about 0.01 wt % to about 2.5 wt %. In still another aspect, the secondary antioxidant is present in an amount from about 0.5 wt % to about 2.5 wt %. In yet another aspect, the secondary antioxidant is present in an amount from about 0.5 wt % to about 2.0 wt %. In still another aspect, the secondary antioxidant is present in an amount from about 0.05 wt % to about 0.4 wt %. In still another aspect, the secondary antioxidant is present in an amount from about 0.05 wt % to about 0.2 wt %. In a yet further aspect, the secondary anti-oxidant is present in an amount from about 0.01 wt % to about 0.50 wt %. In an even further aspect, the secondary anti-oxidant is present in an amount from about 0.05 wt % to about 0.25 wt %.

In various aspects, the thermoplastic composition can further comprise a hydrolytic stabilizer, wherein the hydrolytic stabilizer comprises a hydrotalcite and an inorganic buffer salt. In a further aspect, the thermoplastic composition comprises a hydrolytic stabilizer, wherein the hydrolytic stabilizer comprises one or more hydrotalcites and an inorganic buffer salt comprising one or more inorganic salts capable of pH buffering. Either synthetic hydrotalcites or natural hydrotalcites can be used as the hydrotalcite compound in the present disclosure. Exemplary hydrotalcites that are useful in the compositions of the present are commercially available and include, but are not limited to, magnesium hydrotalcites such as DHT-4C (available from Kyowa Chemical Co.); Hysafe 539 and Hysafe 530 (available from J.M. Huber Corporation).

In a further aspect, suitable thermal stabilizer additives include, for example, organic phosphites such as triphenyl phosphite, tris-(2,6-dimethylphenyl)phosphite, tris-(mixed mono- and di-nonylphenyl)phosphite or the like; phosphonates such as dimethylbenzene phosphonate or the like, organic phosphates such as trimethyl phosphate, thioesters such as pentaerythritol betalaurylthiopropionate, and the like, or combinations comprising at least one of the foregoing thermal stabilizers.

Thermal stabilizers are generally used in amounts of about 0.01 wt % to about 5 wt %, optionally about 0.05 wt % to about 2.0 wt % of the composition. In one aspect, the thermal stabilizer is present in an amount from about 0.01 wt % to about 3.0 wt %. In another aspect, the thermal stabilizer is present in an amount from about 0.01 wt % to about 2.5 wt %. In still another aspect, the thermal stabilizer is present in an amount from about 0.5 wt % to about 2.5 wt %. In still another aspect, the thermal stabilizer is present in an amount from about 0.5 wt % to about 2.0 wt %. In still another aspect, the thermal stabilizer is present in an amount from about 0.1 wt % to about 0.8 wt %. In still another aspect, the thermal stabilizer is present in an amount from about 0.1 wt % to about 0.7 wt %. In still another aspect, the thermal stabilizer is present in an amount from about 0.1 wt % to about 0.6 wt %. In still another aspect, the thermal stabilizer is present in an amount from about 0.1 wt % to about 0.5 wt %. In still another aspect, the thermal stabilizer is present in an amount from about 0.1 wt % to about 0.4 wt %. In still another aspect, the thermal stabilizer is present in an amount from about 0.05 wt % to about 1.0 wt %.

In various aspects, the UV additive can comprise hindered amines. Hindered amines are used to make the ultraviolet radiation stable in the polymer compositions. The sterically hindered amine (HALS) are blended into the polymer compositions described herein and have the structure of Formula:

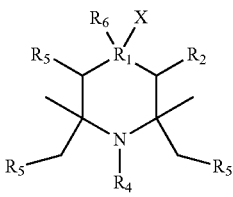

wherein $R^1$ is C, X is H, and $R^2$ is H; wherein R.sub.4 is selected from hydrogen, oxyl, hydroxyl, alkyl of 1 to 20 carbons, alkenyl or alkynyl of 3 to 8 carbons, aralkyl of 7 to 12 carbons, aliphatic acyl of 1 to 10 carbons, aromatic acyl of 7 to 13 carbons, alkoxycarbonyl of 2 to 9 carbons, aryloxycarbonyl of 7 to 15 carbons, alkyl, aryl, cycloalkyl or aralkyl substituted carbamoyl of 2 to 13 carbons, hydroxyalkyl of 1 to 5 carbons, 2-cyanoethyl, epoxyalkyl of 3 to 10 carbons, or a polyalkylene oxide group of 4 to 30 carbons; R.5 is selected from hydrogen or alkyl of 1 to 4 carbons; R6 is selected from hydrogen, hydroxyl, alkoxy of 1 to 4 carbons,

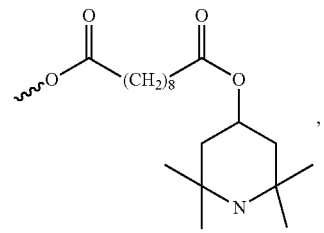

when $R_6$ is hydrogen, X is a divalent radical selected from —Z—$R_7$—C(=O)—N($R_8$)—, —Z—C(=O)—N($R_8$)—, —Z—C(=O)—$R_9$—C(=O)—N($R_8$)—, —$R_7$—C(=O)—N($R_8$)—, or —C(=O)—N($R_8$)—, Z is —O—, —N($R_{10}$)—, or —N($R_{12}$)—R11-N($R_{12}$)—; when $R_6$ is hydroxyl or alkoxy, X is a divalent radical selected from —R7-C(=O)—N(R8)- or —C(=O)—N(R8)-, R7 is an alkylene diradical of 1 to 4 carbons, R8 is selected from hydrogen, primary or secondary alkyl of 1 to 8 carbons, aralkyl of 7 to 12 carbons, or cycloalkyl of 5 to 12 carbons, R9 is selected from a direct bond or the following substituted or unsubstituted radicals of alkylene of 1 to 14 carbons, oxydialkylene of 4 to 10 carbons, thiodialkylene of 4 to 10 carbons, alkenylene of 2 to 10 carbons, o, m, or p-phenylene, wherein the substituents for R9 are selected from lower alkyl, lower alkoxy, hydroxy, bromine, chlorine, mercapto, or lower alkylmercapto; R10 and R12 are selected from hydrogen, alkyl of 1 to 10 carbons, aryl of 6 to 12 carbons, aralkyl of 7 to 12 carbons, and cycloalkyl of 5 to 12 carbons, R10 may be a radical of 2-cyanoethyl radical or the formula; R11 is alkylene of 2 to 12 carbons.

HALS bearing reactive hydrazide include the following: 3-(2,2,6,6-tetramethyl-4-piperidinylamino)propionhydrazide, 3-(1,2,2,6,6-pentamethyl-4-piperidinylamino)propionhydrazide, (2,2,6,6-tetramethyl-4-piperidinylamino)acetylhydrazide, (1,2,2,6,6-pentamethyl-4-piperidinylamino)acetylhydrazide, N-(2,2,6,6-tetramethyl-4-piperidinyl)hydrazinecarboxamide, N-(1,2,2,6,6-pentamethyl-4-piperidinyl)hydrazinecarboxamide, N-(2,2,6,6-tetramethyl-4-piperidinyl)-N'-aminooxamide, N-(1,2,2,6,6-pentamethyl-4-piperidinyl)-N'-aminooxamide, N-(2,2,6,6-tetramethyl-4-piperidinyl)-N'-aminosuccinamide, N-(1,2,2,6,6-pentamethyl-4-piperidinyl)-N'-aminosuccinamide, N-(2,2,6,6-tetramethyl-4-piperidinyl)-N'-aminomalonamide, N-(1-benzyl-2,2,6,6-tetramethyl-4-piperidinyl)-N'-aminomalonamide, N-(1-benzyl-2,2,6,6-tetramethyl-4-piperidinyl)-N'-aminooxamide, N-(1-beta-hydroxyethyl-2,2,6,6-tetramethyl-4-piperidinyl)-N'-aminooxamide, N-(2,6-diethyl-2,3,6-trimethyl-4-piperidinyl)-N'-aminoadipamide, N-(1-acetyl-2,2,6,6-tetramethyl-4-piperidinyl)-N'-aminooxamide, 3-(1-acetyl-2,2,6,6-tetramethyl-4-piperidinylamino)propionhydrazide, (2,2,6,6-tetramethyl-4-piperidinyloxy)acetyl hydrazide, (1,2,2,6,6-pentamethyl-4-piperidinyloxy)acetylhydrazide, 3-(2,2,6,6-tetramethyl-4-piperidinyloxy)propionhydrazide, 3,(1,2,2,6,6-pentamethyl-4-piperidinyloxy)propionhydrazide, N-(1-acetyl-2,2,6,6-tetramethyl-4-piperidinyl)hydrazinecarboxamide, N-(1-benzoyl-2,2,6,6-tetramethyl-4-piperidinyl)-N'-aminooxamide, 3-(1-benzoyl-2,2,6,6-tetramethyl-4-piperidinylamino)propionhydrazide, N,N-bis-(2,2,6,6-tetramethyl-4-piperidinyl)-N'-aminooxamide, and 3-[N,N-bis-(2,2,6,6-tetramethyl-4-piperidinyl)amino]propionhydrazide.

In a further aspect, the HALS described above act as stabilizers because they are readily oxidized to the nitroxyl radical, which acts as a catalyst for the termination step of the free radical oxidation cycle. These HALS are also good catalysts and are consumed slowly so they greatly increase the stability of polycarbonate which have slow initiation steps and very long kinetic chains for the oxidation cycle.

In a further aspect, the HALS may be added to the polymerization reaction prior to extrusion. The polymerization reaction may include one or more structural HAL units in the presence of one or more copolymers.

In a further aspect, HALS may be present in the composition at a weight percent below 0.5%, below 0.4%, below 0.3%, below 0.2%, below 0.1%, below 0.007%, or below 0.005%. The HALS may be present in the composition at a weight percent below 0.3%. A single HALS compound may have a molecular weight below 3000 g/mol, below 2500 g/mol, below 2000 g/mol, below 1870 g/mol, below 1700 g/mol, below 1600 g/mol, below 1530 g/mol, below 1500 g/mol, below 1000 g/mol, below 750 g/mol, below 500 g/mol, below 250 g/mol, or below 100 g/mol. The molecular weight, or molecular mass, may be calculated from the structure of the HALS compound.

In a further aspect, the additive can comprise a UV stabilizer for improved performance in UV stabilization. UV stabilizers disperse the UV radiation energy by absorbing the energy through reversible chemical rearrangements such as hydrogen shifts.

In a further aspect, UV stabilizers may be hydroxybenzophenones, hydroxyphenyl benzotriazoles, cyanoacrylates, oxanilides, and hydroxyphenyl triazines. UV stabilizers may include, but are not limited to, poly[(6-morphilino-s-triazine-2,4-diyl)[2,2,6,6-tetramethyl-4-piperidyl)imino]-hexamethylene[(2,2,6,6-tetramethyl-4-piperidyl)imino], 2-hydroxy-4-octloxybenzophenoe (UVINUL® 3008), 6-tert-butyl-2-(5-chloro-2H-benzotriazole-2-yl)-4-methylphenyl (UVINUL® 3026), 2,4-di-tert-butyl-6-(5-chloro-2H-benzotriazole-2-yl)-phenol (UVINUL® 3027), 2-(2H-benzotriazole-2-yl)-4,6-di-tert-pentylphenol (UVINUL® 3028), 2-(2H-benzotriazole-2-yl)-4-(1,1,3,3-tetramethylbutyl)-phenol (UVINUL® 3029), 1,3-bis[(2'cyano-3',3'-diphenylacryloyl)oxy]-2,2-bis-{[(2'-cyano-3',3'-diphenylacryloyl)oxy]methyl}-propane (UVINUL® 3030), 2-(2H-benzotriazole-2-yl)-4-methylphenol (UVINUL® 3033), 2-(2H-bezhotriazole-2-yl)-4,6-bis(1-methyl-1-phenyethyl)phenol (UVINUL® 3034), ethyl-2-cyano-3,3-diphenylacrylate (UVINUL® 3035), (2-ethylhexyl)-2-cyano-3,3-diphenylacrylate (UVINUL® 3039), N,N'-bisformyl-N,N'-bis(2,2,6,6-tetramethyl-4-piperidinyl) hexamethylenediamine (UVINUL® 4050H), bis-(2,2,6,6-tetramethyl-4-piperidyl)-sebacate (UVINUL® 4077H), bis-(1,2,2,6,6-pentamethyl-4-piperidyl)-sebacate+methyl-(1,2,2,6,6-pentamethyl-4-piperidyl)-sebacate (UVINUL® 4092H) or combination thereof.

In a further aspect, the UV stabilizer may be benzotriazoles. Benzotriazoles have the general structure of formula:

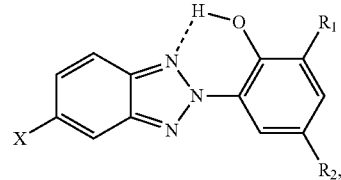

wherein R1 is selected from the group consisting of hydrogen, alkyl, aryl, substituted alkyls, substituted aryls and R2 is selected from the group consisting of hydrogen, alkyl, aryl, substituted alkyls, substituted aryls. Benzotriazoles have absorbance maxima at about 295 nm ($\epsilon$~14,000) and 345 nm ($\epsilon$~16,000). Benzotriazoles may have a fairly sharp cutoff in absorbance maxima so that there is little tailing into the visible and little yellow color. These compounds may also be substituted adjacent to the hydroxyl group to increase steric hinderance and ensure that the polymer does not contain basic residues that catalyze transesterification with polycarbonates. Exemplary, non-limiting, benzotriazole UV stabilizers include CYASORB® 5411 or TINUVIN® 234.

In a further aspect, the UV stabilizer can be a benzophenone. Benzophenones have the general structure of formula:

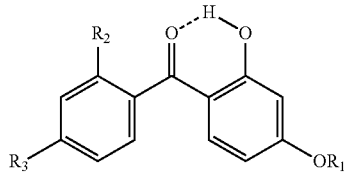

wherein R2 is any one of the following hydrogen, alkyl, aryl, substituted alkyls, substituted aryls and R3 is any one of the following hydrogen, alkyl, aryl, substituted alkyls, substituted aryls. Benzophenones have absorbance maxima at about 285 nm ($\epsilon$~15,000) and 325 nm ($\epsilon$~10,000). Benzophenones have a long tail in absorbance maxima and create a slightly yellow color in compounds containing benzophenones. The benzophenones may have a 2-hydroxy group and an alkoxy or hydroxyl group in the 4 position. Both of these groups reduce colorization and provide good photostability. The most common derivatives of benzophenones are the 4-methoxy and 4-octyloxy esters. Exemplary, non-limiting, benzophenone UV stabilizers include CYASORB® 24, UVINUL® 3049 and UVINUL® 3050.

In a further aspect, the UV stabilizer can be a cyanoacrylate. Cyanoacrylates have the general structure of formula:

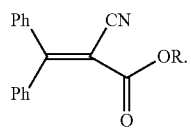

Cyanoacrylates have a single absorbance maximum at about 300 nm ($\epsilon$~15,000) resulting in less absorption at longer wavelengths than benzotriazoles or benzophenones. Exemplary, non-limiting, examples of cyanoacrylate UV stabilizers include UVINUL® 3030 and UVINUL® 3059. UVINUL® 3030 is a UV absorber form BASF with the chemical name 1,3-bis-[2'-cyano-3 '3 {[2-cyano-3',3'-diphenylacryloyboxy]methyl}propan. UVINUL® 5050H is an oligomeric sterically hindered amine from BASF. Its molecular weight is approximately 3500 g/mol.

In a further aspect, the UV stabilizer can be a triazine. Triazines have the general structure of formula:

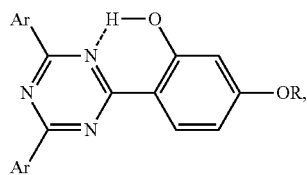

wherein R is an alkyl, substituted alkyl. Triazines have an absorption maxima at 290 nm ($\epsilon$~43,000) and at about 340 nm ($\epsilon$~23,500). Triazines have a high extinction coefficient and high molecular weights. Exemplary triazine UV stabilizers include, but not limited to TINUVIN® 400, CYASORB® 1164L and TINUVIN® 234.

In a further aspect, the UV stabilizer can be an oxanilide. Oxanilides have the general structure of formula:

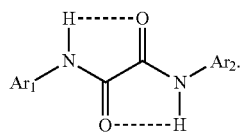

Oxanilides have similar absorption characteristics as cyanoacrylates and may be asymmetrically substituted to broaden the absorption band and improve solubility.

In a further aspect, the antioxidant is a primary antioxidant, a secondary antioxidant, or combinations thereof. In a still further aspect, the primary antioxidant is selected from a hindered phenol and secondary aryl amine, or a combination thereof. In yet a further aspect, the hindered phenol comprises one or more compounds selected from triethylene glycol bis[3-(3-t-butyl-5-methyl-4-hydroxyphenyl)propionate], 1,6-hexanediol bis[3-(3,5-di-t-butyl-4-hydroxyphenyl)propionate], 2,4-bis(n-octylthio)-6-(4-hydroxy-3,5-di-t-butylanilino)-1,3,5-triazine, pentaerythrityl tetrakis[3-(3,5-di-t-butyl-4-hydroxyphenyl)propionate], 2,2-thiodiethylene bis[3-(3,5-di-t-butyl-4-hydroxyphenyl)propionate], octadecyl 3-(3,5-di-t-butyl-4-hydroxyphenyl)propionate, N,N'-hexamethylene bis(3,5-di-t-butyl-4-hydroxy-hydrocinnamamide), tetrakis(methylene 3,5-di-tert-butyl-hydroxycinnamate) methane, and octadecyl 3,5-di-tert-butylhydroxyhydrocinnamate. In an even further aspect, the hindered phenol comprises octadecyl-3-(3,5-di-t-butyl-4-hydroxyphenyl)-propionate.

In various aspects, plasticizers, lubricants, and/or mold release agents additives can also be used. There is a considerable overlap among these types of materials, which include, for example, phthalic acid esters such as dioctyl-4,5-epoxy-hexahydrophthalate; tris(octoxycarbonylethyl)isocyanurate; tristearin; di- or polyfunctional aromatic phosphates such as resorcinol tetraphenyl diphosphate (RDP), the bis(diphenyl) phosphate of hydroquinone and the bis(diphenyl)phosphate of bisphenol-A; poly-alpha-olefins; epoxidized soybean oil; silicones, including silicone oils; esters, for example, fatty acid esters such as alkyl stearyl esters, e.g. methyl stearate; stearyl stearate, pentaerythritol tetrastearate, and the like; mixtures of methyl stearate and hydrophilic and hydrophobic nonionic surfactants comprising polyethylene glycol polymers, polypropylene glycol polymers, and copolymers thereof; waxes such as beeswax, montan wax, paraffin wax or the like.

Thermoplastic composition additives such as plasticizers, lubricants, and/or mold release agents additive are generally used in amounts of about 0.01 wt % to about 20 wt %, optionally about 0.5 wt % to about 10 wt % the polycarbonate blend composition. In one aspect, the mold release agent is methyl stearate; stearyl stearate or pentaerythritol tetrastearate. In another aspect, the mold release agent is pentaerythritol tetrastearate.

In various aspects, the mold release agent is present in an amount from about 0.01 wt % to about 3.0 wt %. In another aspect, the mold release agent is present in an amount from about 0.01 wt % to about 2.5 wt %. In still another aspect, the mold release agent is present in an amount from about 0.5 wt % to about 2.5 wt %. In still another aspect, the mold release agent is present in an amount from about 0.5 wt % to about 2.0 wt %. In still another aspect, the mold release agent is present in an amount from about 0.1 wt % to about 0.6 wt %. In still another aspect, the mold release agent is present in an amount from about 0.1 wt % to about 0.5 wt %.

In a further aspect, the additive can comprise a phosphorous-containing additive, such as a phosphite or a phosphate. In some aspects, the one or more additive comprises a phosphite. In further aspects, the phosphite comprises a diphenyl alkyl phosphite, phenyl dialkyl phosphite, trialkyl phosphite, dialkyl phosphite, triphenyl phosphite, diphenyl pentaerythritol diphosphite, or any combination thereof. In other aspects, the additive comprises at least one phosphorus compound. In further aspects, the phosphorus compound comprises an aryl phosphate comprising triphenyl phosphate, resorcinol phenyl diphosphate, spirobiindane phenyl diphosphate, di-tertbutyl hydroquinone phenyl diphosphate, biphenol phenyl diphosphate, hydroquinone phenyl diphosphate, or a combination thereof.

According to aspects of the disclosure, the amount of phosphorous-containing compound compounded with the polycarbonate is an amount sufficient to result in the desired effect for which the additive is intended. For example, if the additive is a flame retardant the amount of additive will be that amount sufficient to provide a desired level of flame retardance. Such amounts can be readily determined by one of ordinary skill in the art without undue experimentation. In some aspects, where the phosphorous-containing compound is a phosphite, phosphonate or combination thereof, it is present in an amount in the range of 0.0001 to 2.0 wt % based on the parts by weight of the polymer composition.

In various aspects, the thermoplastic composition can optionally comprise a flame retardant, wherein the flame retardant can comprise any flame retardant material or mixture of flame retardant materials suitable for use in the inventive polymer compositions. In one aspect, the thermoplastic compositions of the present disclosure do not comprise a flame retardant.

In various aspects, the flame retardant is a phosphorus-containing flame retardant. In a further aspect, the flame retardant is selected from an oligomeric phosphate flame retardant, polymeric phosphate flame retardant, an aromatic polyphosphate flame retardant, oligomeric phosphonate flame retardant, phenoxyphosphazene oligomeric flame retardant, or mixed phosphate/phosphonate ester flame retardant compositions.

In a further aspect, the thermoplastic compositions comprise a flame retardant that is a non-brominated and non-chlorinated phosphorous-containing compound such as an organic phosphate. Exemplary organic phosphates can include an aromatic phosphate of the formula $(GO)_3P=O$, wherein each G is independently an alkyl, cycloalkyl, aryl, alkaryl, or aralkyl group, provided that at least one G is an aromatic group. Two of the G groups can be joined together to provide a cyclic group, for example, diphenyl pentaerythritol diphosphate, which is described by Axelrod in U.S. Pat. No. 4,154,775. Other suitable aromatic phosphates can be, for example, phenyl bis(dodecyl)phosphate, phenyl bis(neopentyl)phosphate, phenyl bis(3,5,5'-trimethylhexyl)phosphate, ethyl diphenyl phosphate, 2-ethylhexyl di(p-tolyl)phosphate, bis(2-ethylhexyl)p-tolyl phosphate, tritolyl phosphate, bis(2-ethylhexyl)phenyl phosphate, dibutyl phenyl phosphate, 2-chloroethyl diphenyl phosphate, p-tolyl bis(2,5,5'-trimethylhexyl)phosphate, 2-ethylhexyl diphenyl phosphate, or the like. A specific aromatic phosphate is one in which each G is aromatic, for example, triphenyl phosphate, tricresyl phosphate, isopropylated triphenyl phosphate, and the like.

In a further aspect, di- or polyfunctional aromatic phosphorous-containing compounds can also be present. Examples of suitable di- or polyfunctional aromatic phosphorous-containing compounds include triphenyl phosphate (TPP), resorcinol tetraphenyl diphosphate (RDP), the bis(diphenyl)phosphate of hydroquinone and the bis(diphenyl) phosphate of bisphenol-A, respectively, their oligomeric and polymeric counterparts, and the like.

In a further aspect, the flame retardant can be an organic compounds containing phosphorous-nitrogen bonds. For example, phosphonitrilic chloride, phosphorous ester amides, phosphoric acid amides, phosphonic acid amides, phosphinic acid amides, tris(aziridinyl)phosphine oxide, or the like. In one aspect, a phenoxyphosphazene is used as a flame retardant.

In a further aspect, the phosphorus-containing flame retardant is selected from a phosphine, a phosphine oxide, a bisphosphine, a phosphonium salt, a phosphinic acid salt, a phosphoric ester, and a phosphorous ester.

In a further aspect, the phosphorus-containing flame retardant is selected from rescorcinol bis(diphenyl phosphate), resorcinol bis(dixylenyl phosphate), hydroquinone bis(diphenyl phosphate), bisphenol-A bis(diphenyl phosphate), 4,4'-biphenol bis(diphenyl phosphate), triphenyl phosphate, methylneopentyl phosphite, pentaerythritol diethyl diphosphite, methyl neopentyl phosphonate, phenyl neopentyl phosphate, pentaerythritol diphenyldiphosphate, dicyclopentyl hypodiphosphate, dineopentyl hypophosphite, phenylpyrocatechol phosphite, ethylpyrocatechol phosphate and dipyrocatechol hypodiphosphate. In a still further aspect, the flame retardant is selected from triphenyl phosphate; cresyldiphenylphosphate; tri(isopropylphenyl)phosphate; resorcinol bis(diphenylphosphate); and bisphenol-A bis(diphenyl phosphate). In a yet further aspect, resorcinol bis(biphenyl phosphate), bisphenol A bis(diphenyl phosphate) hydroquinone bis(diphenyl phosphate), phosphoric acid, 1,3-phenylene tetraphenyl ester), bis-phenol-A bis-diphenyl phosphate) or mixtures thereof. In an even further aspect, the flame retardant is bisphenol-A bis(diphenyl phosphate). In a still further aspect, the phosphorus-containing flame retardant is selected from resorcinol bis(biphenyl phosphate), bisphenol A bis(diphenyl phosphate), and hydroquinone bis(diphenyl phosphate), or mixtures thereof. In yet a further aspect, the phosphorus-containing flame retardant is bisphenol A bis (diphenyl phosphate). In an even further aspect, the phosphorus-containing flame retardant is resorcinol bis(biphenyl phosphate).

In a further aspect, the flame retardant is present in an amount from greater than about 0 wt % to about 15 wt %. In a still further aspect, the flame retardant is present in an amount from about 0.01 wt % to about 15 wt %. In a yet further aspect, the flame retardant is present in an amount from about 0.1 wt % to about 15 wt %. In an even further aspect, the flame retardant is present in an amount from about 1 wt % to about 15 wt %.

In a further aspect, the flame retardant is present in an amount from about 1 wt % to about 1 wt %. In a still further aspect, the flame retardant is present in an amount from about 1 wt % to about 13 wt %. In yet a further aspect, the flame retardant is present in an amount from about 1 wt % to about 12 wt %. In an even further aspect, the flame retardant is present in an amount from about 2 wt % to about 12 wt %. In a still further aspect, the flame retardant is present in an amount from about 3 wt % to about 12 wt %. In yet a further aspect, the flame retardant is present in an amount from about 4 wt % to about 12 wt %. In an even further aspect, the flame retardant is present in an amount from about 4 wt % to about 11 wt %. In a still further aspect, the flame retardant is present in an amount from about 4 wt % to about 10 wt %. In yet a further aspect, the flame retardant is present in an amount from about 5 wt % to about 10 wt %. In an even further aspect, the flame retardant is present in an amount from about 6 wt % to about 10 wt %.

In a further aspect, anti-drip agents can also be present. In a further aspect, the anti-drip agent is a styrene-acrylonitrile copolymer encapsulated polytetrafluoroethylene. Exemplary anti-drip agents can include a fibril forming or non-fibril forming fluoropolymer such as polytetrafluoroethylene (PTFE). The anti-drip agent can optionally be encapsulated by a rigid copolymer, for example styrene-acrylonitrile (SAN). PTFE encapsulated in SAN is known as TSAN. Encapsulated fluoropolymers can be made by polymerizing the encapsulating polymer in the presence of the fluoropolymer, for example, in an aqueous dispersion. TSAN can provide significant advantages over PTFE, in that TSAN can be more readily dispersed in the composition. A suitable TSAN can comprise, for example, about 50 wt % PTFE and about 50 wt % SAN, based on the total weight of the encapsulated fluoropolymer. Alternatively, the fluoropolymer can be pre-blended in some manner with a second polymer, such as for, example, an aromatic polycarbonate resin or SAN to form an agglomerated material for use as an anti-drip agent. Either method can be used to produce an encapsulated fluoropolymer.

In a further aspect, the anti-drip agent is present in an amount from about 0.01 wt % to about 3 wt %. In a still further aspect, the anti-drip agent is present in an amount from about 0.01 wt % to about 2.5 wt %. In yet a further aspect, the anti-drip agent is present in an amount from about 0.5 wt % to about 2.0 wt %.

In various aspects, the thermoplastic compositions of the present disclosure can optionally further comprise reinforcing fillers in addition to one or more glass fiber fillers as described herein above. For example, suitable fillers or reinforcing agents include any materials known for these uses, provided that they do not adversely affect the desired properties. For example, suitable fillers and reinforcing agents include silicates and silica powders such as aluminum silicate (mullite), synthetic calcium silicate, zirconium silicate, fused silica, crystalline silica graphite, natural silica sand, or the like; boron powders such as boron-nitride powder, boron-silicate powders, or the like; oxides such as $TiO_2$, aluminum oxide, magnesium oxide, or the like; calcium sulfate (as its anhydride, dehydrate or trihydrate); calcium carbonates such as chalk, limestone, marble, synthetic precipitated calcium carbonates, or the like; talc, including fibrous, modular, needle shaped, lamellar talc, or the like; wollastonite; surface-treated wollastonite; glass spheres such as hollow and solid glass spheres, silicate spheres, cenospheres, aluminosilicate (armospheres), or the like; kaolin, including hard kaolin, soft kaolin, calcined kaolin, kaolin comprising various coatings known in the art to facilitate compatibility with the polymeric matrix resin, or the like; single crystal fibers or "whiskers" such as silicon carbide, alumina, boron carbide, iron, nickel, copper, or the like; fibers (including continuous and chopped fibers) such as asbestos, carbon fibers; sulfides such as molybdenum sulfide, zinc sulfide, or the like; barium compounds such as barium titanate, barium ferrite, barium sulfate, heavy spar, or the like; metals and metal oxides such as particulate or fibrous aluminum, bronze, zinc, copper and nickel, or the like; flaked fillers such as glass flakes, flaked silicon carbide, aluminum diboride, aluminum flakes, steel flakes or the like; fibrous fillers, for example short inorganic fibers such as those derived from blends comprising at least one of aluminum silicates, aluminum oxides, magnesium oxides, and calcium sulfate hemihydrate or the like; natural fillers and reinforcements, such as wood flour obtained by pulverizing wood, fibrous products such as kenaf, cellulose, cotton, sisal, jute, flax, starch, corn flour, lignin, ramie, rattan, agave, bamboo, hemp, ground nut shells, corn, coconut (coir), rice grain husks or the like; organic fillers such as polytetrafluoroethylene, reinforcing organic fibrous fillers formed from organic polymers capable of forming fibers such as poly(ether ketone), polyimide, polybenzoxazole, poly(phenylene sulfide), polyesters, polyethylene, aromatic polyamides, aromatic polyimides, polyetherimides, polytetrafluoroethylene, acrylic resins, poly(vinyl alcohol) or the like; as well as additional fillers and reinforcing agents such as mica, clay, feldspar, flue dust, fillite, quartz, quartzite, perlite, Tripoli, diatomaceous earth, carbon black, or the like, or combinations comprising at least one of the foregoing fillers or reinforcing agents. In a still further aspect, the filler is talc, glass fiber, kenaf fiber, or combinations thereof. In yet a further aspect, the filler is glass fiber. The fillers and reinforcing agents can be coated with a layer of metallic material to facilitate conductivity, or surface treated with silanes, siloxanes, or a combination of silanes and siloxanes to improved adhesion and dispersion with the polymeric matrix resin.

In a further aspect, the additional reinforcing filler is selected from carbon fiber, a mineral filler, or combinations thereof. In a still further aspect, the reinforcing filler is selected from mica, talc, clay, wollastonite, zinc sulfide, zinc oxide, carbon fiber, ceramic-coated graphite, titanium dioxide, or combinations thereof.

In one aspect, the present disclosure provide a thermoplastic composition comprising a polyester composition comprising the reaction product of: a) a dicarboxylic acid component comprising phenylindane dicarboxylic acid (PIDA); b) a diol component; at least one catalyst present in and amount of from about 50 ppm to about 300 ppm; wherein the polyester composition exhibits a Tg of at least about 107° C.; wherein the polyester composition exhibits an intrinsic viscosity of at least about 0.7 dl/g; and wherein the polyester composition has a lead content of less than about 10 ppm.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present disclosure is not entitled to antedate such publication by virtue of prior disclosure. Further, the dates of publication provided herein can be different from the actual publication dates, which can require independent confirmation.

D. Aspects

The present disclosure comprises at least the following aspects.

Aspect 1: A method for preparing a phenylindane dicarboxylic acid (PIDA) monomer, the method comprising: reacting an alkylstyrene under first reaction conditions effective to provide a first reaction product comprising at least one phenylindane; and reacting the first reaction product under second reaction conditions effective to provide a second reaction product comprising at least one phenylindane dicarboxylic acid (PIDA) monomer.

Aspect 2: The method of aspect 1, wherein the phenylindane dicarboxylic acid monomer does not exhibit a half maximal inhibitory concentration ($IC_{50}$) less than 0.00025M for alpha or beta in vitro estradiol receptors.

Aspect 3: The method of any of aspects 1-2, wherein the alkylstyrene has a structure represented by the formula:

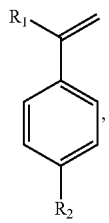

wherein each of R1 and R2 is each independently selected from hydrogen and C1-C3 alkyl.

Aspect 4: The method of any of aspects 1-2, wherein the alkylstyrene is alpha-methylstyrene (AMS).

Aspect 5: The method of any of aspects 1-2, wherein the alkylstyrene is α-p-dimethylstyrene.

Aspect 6: The method of any of aspects 1-2, wherein the phenylindane is trimethyl phenylindane.

Aspect 7: The method of any of aspects 1-6, wherein the phenylindane is tetramethyl phenylindane.

Aspect 8: The method of any of aspects 1-7, further comprising the step of reacting limonene to provide the the alkylstyrene.

Aspect 9: The method of any of aspects 1-7, further comprising the step of reacting an alkylbenzene to provide the alkylstyrene.

Aspect 10: The method of aspect 9, wherein the alkylbenzene is p-cymene or p-bromo toluene, or a combination thereof.

Aspect 11: The method of any of aspects 1-7, further comprising the step of reacting an acetophenone to provide the alkylstyrene.

Aspect 12: The method of aspect 101, wherein the acetophenone is reacted in the presence of a Grignard reagent.

Aspect 13: The method of aspect 12, wherein the Grignard reagant is methyl magnesium bromide.

Aspect 14: The method of any of aspects 1-13, wherein the phenylindane dicarboxylic acid monomer has a structure represented by the formula:

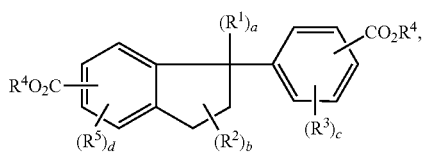

wherein $R^1$, $R^2$, $R^3$, and $R^5$ are each independently a C1-C3 alkyl group, a is 0-1, b is 0-4, c is 0-4 and d is 0-3, and each $R^4$ is independently a hydrogen or a C1-C3 alkyl group.

Aspect 15: The method of any of aspects 1-2, wherein the phenylindane dicarboxylic acid monomer has a structure represented by the formula

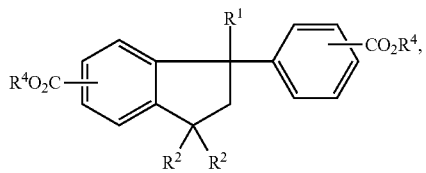

wherein each $R^4$ is independently hydrogen or a C1-C3 alkyl group.

Aspect 16: The method of any of aspects 1-2, wherein the phenylindane dicarboxylic acid monomer has a structure represented by the formula:

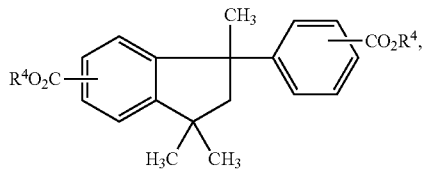

wherein wherein each $R^4$ is independently hydrogen or a C1-C3 alkyl group.

Aspect 17: The method of any of aspects 1-2, wherein the phenylindane dicarboxylic acid monomer is 3-(4-carboxyphenyl)-1,1,3-trimethyl-5-indan carboxylic acid, 3-(4-carboxyphenyl)-1,3-diethyl-1-methyl-5-indan carboxylic acid, or 3-(4-carboxyphenyl)-1,3-dipropyl-1-methyl-5-indan carboxylic acid.

Aspect 18: The method of any of aspects 1-2, wherein the phenylindane dicarboxylic acid monomer is this monomer is as 1,3,3-trimethyl-1-phenylindan-4',5-dicarboxylic acid.

Aspect 19: The method of any of aspects 1-2, wherein the first conditions comprise reacting the alkylstyrene in the presence of a catalyst.

Aspect 20: The method of aspect 19, wherein the catalyst comprises an acid catalyst, ion exchange resin catalyst, or a combination thereof.

Aspect 21: The method of aspect 20, wherein the acid catalyst acid comprises hydrochloric acid, sulfuric acid or nitric acid, a combination thereof.

Aspect 22: The method of any of aspects 1-21, wherein the first or second reaction conditions comprise adjusting the temperature to at least about 40° C.

Aspect 23: The method of any of aspects 1-21, wherein the first or second reaction conditions comprise adjusting the temperature in the range of from about 40° C. to about 250° C.

Aspect 24: The method of any of aspects 1-21, wherein the first or second reaction conditions comprise maintaining the reaction for at least about 1 hours.

Aspect 25: The method of any of aspects 1-2, further comprising reacting the first reaction product to provide a reaction product comprising at least one acetylated phenylindane.

Aspect 26: The method of aspect 25, wherein reacting is acetylating with an acetylating agent in the presence of a Friedel-Crafts catalyst to provide reaction product comprising an isomer mixture.

Aspect 27: The method of aspect 26, wherein the acetylating agent is acetyl chloride, chloroacetyl chloride or acetic anhydride, or a combination thereof.

Aspect 28: The method of aspect 26, wherein the Friedel-Crafts catalyst comprises aluminum chloride, zinc chloride, or iron(III) chloride, or a combination thereof.

Aspect 29: The method of aspect 23, wherein the acetylated phenylindane is diacetyl phenylindane.

Aspect 30: The method of any of aspects 1-29, wherein the second reaction conditions comprise oxidative reaction conditions.

Aspect 31: The method of any of aspects 1-29, wherein the second conditions comprise reacting the first reaction product in the presence of an oxidizing agent.

Aspect 32: The method of aspect 31, wherein the oxidizing agent comprises: chromic anhydride(CrO3); oxygen containing heavy metals comprising one or more of manganese, cobalt, lead, iron, nickel, copper, and vanadium; or oxides of one or more of manganese, cobalt, lead, iron, nickel, copper, and vanadium; or a combination thereof.

Aspect 33: The method of any of aspects 1-29, wherein the second conditions comprise reacting the first reaction product in the presence of $KMnO_4$ and pyridine.

Aspect 34: The method of any of aspects 1-29, wherein the first reaction product comprises at least about 50 wt % of phenylindane.

Aspect 35: The method of any of aspects 1-29, wherein the second reaction product comprises at least about 50 wt % of phenylindane dicarboxylic acid.

Aspect 36: The method of any of aspects 1-29, wherein the method provides a final yield of phenylindane dicarboxylic acid of at least about 60%.

Aspect 37: The method of any of aspects 1-36, further comprising purifying the second reaction product under conditions effective to provide a reaction product comprising at least 90 wt % PIDA.

Aspect 38: The method of aspect 37, further comprising the step of filtering, separating, washing, or drying, or a combination thereof.

Aspect 39: The method of aspect 37, wherein purifying comprises dissolving the reaction product using aqueous NaHCO3 solution or glacial acetic acid, or a combination thereof.

Aspect 40: The method of aspect 37, wherein purifying comprises adjusting the pH of reaction product to a pH effective to provide a solid reaction product.

Aspect 41: The method of any of aspects 1-40, further comprising separating of the second reaction product.

Aspect 42: The method of aspect 41, wherein the separating comprises chiral separation of a racemic mixture of monomers using high pressure liquid chromatography (HPLC).

Aspect 43: A method for preparing a phenylindane dicarboxylic acid (PIDA) monomer, the method comprising: reacting alphamethylstyrene under first reaction conditions effective to provide a first reaction product comprising at least one phenylindane; acetylating the first reaction product in the presence of a Friedel-Crafts catalyst to provide second reaction product comprising an acetylated phenylindane; and reacting the second reaction product under second reaction conditions effective to provide a second reaction product comprising at least one phenylindane dicarboxylic acid (PIDA) monomer.

Aspect 44: A method for preparing a phenylindane dicarboxylic acid (PIDA) monomer, the method comprising: reacting a alkylbenzene to provide a first reaction product comprising at least one alkylstyrene; reacting the first reaction product under first reaction conditions effective to provide a second reaction product comprising at least one phenylindane; and reacting the second reaction product under second reaction conditions effective to provide a second reaction product comprising at least one phenylindane dicarboxylic acid (PIDA) monomer.

Aspect 45: A polyester composition comprising repeating units derived from at least one PIDA monomer according to aspect 1 and a diol component.

Aspect 46: The polyester composition of aspect 45, wherein the polyester composition is a copolyester comprising repeating ester units derived from the PIDA monomer and at least one additional dicarboxylic acid monomer.

Aspect 47: The polyester composition of aspect 46, wherein the at least one dicarboxylic acid monomer comprises isophthalic acid, terephthalic acid, C6 to C36 aliphatic dicarboxylic acids, furan dicarboxylic acids, naphthalene dicarboxylic acids, sebacic acid, or a combination thereof.

Aspect 48: The polyester composition of aspect 45, wherein the polyester composition is a poly(ester carbonate) comprising repeating ester units derived from the PIDA monomer and at least one phenolic monomer.

Aspect 49: The polyester composition of aspect 48, wherein the phenolic monomer comprises a bisphenolic monomer, a mono phenolic monomer, or a combination thereof.

Aspect 50: A method for preparing a phenylindane dicarboxylic acid monomer, the method comprising: reacting an alkylstyrene under acid catalyzed conditions effective to provide a first reaction product comprising at least one C20 to C32 phenylindane; and reacting the first reaction product under a metal catalyzed oxidation conditions effective to provide a second reaction product comprising a racemic mixture including a phenylindane dicarboxylic acid monomer.

Aspect 51: The method of aspect 50, wherein the phenylindane dicarboxylic acid monomer does not exhibit a half maximal inhibitory concentration ($IC_{50}$) less than 0.00025M for alpha or beta in vitro estradiol receptors.

Aspect 52: The method of aspect 50, wherein the alkylstyrene has a structure represented by the formula:

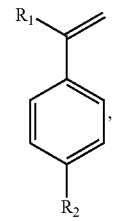

wherein each of R1 and R2 is each independently selected from hydrogen and C1-C3 alkyl.

Aspect 53: The method of aspect 50, wherein the alkylstyrene is alpha-methylstyrene.

Aspect 54: The method of aspect 50, wherein the alkylstyrene is α-p-dimethylstyrene.

Aspect 55: The method of aspect 50, wherein the phenylindane is trimethyl phenylindane.

Aspect 56: The method of aspect 50, wherein the phenylindane is tetramethyl phenylindane.

Aspect 57: The method of aspect 50, further comprising the step of reacting limonene to provide the the alkylstyrene.

Aspect 58: The method of aspect 50, further comprising the step of reacting an alkylbenzene to provide the alkylstyrene.

Aspect 59: The method of aspect 58, wherein the alkylbenzene is p-cymene or p-bromo toluene, or a combination thereof.

Aspect 60: The method of aspect 50, further comprising the step of reacting an acetophenone to provide the alkylstyrene.

Aspect 61: The method of aspect 60, wherein the acetophenone is reacted in the presence of a Grignard reagent.

Aspect 62: The method of aspect 61, wherein the Grignard reagant is methyl magnesium bromide.

Aspect 63: The method of aspect 50, wherein the phenylindane dicarboxylic acid monomer has a structure represented by the formula:

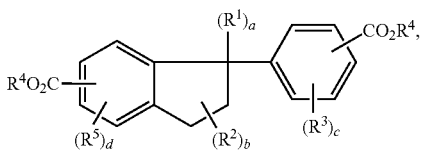

wherein $R^1$, $R^2$, $R^3$, and $R^5$ are each independently a C1-C3 alkyl group, a is 0-1, b is 0-4, c is 0-4 and d is 0-3, and each $R^4$ is independently a hydrogen or a C1-C3 alkyl group.

Aspect 64: The method of aspect 50, wherein the phenylindane dicarboxylic acid monomer has a structure represented by the formula

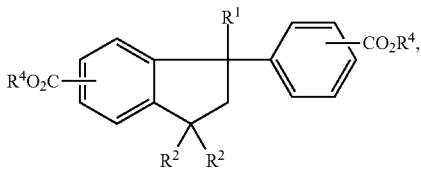

wherein each $R^4$ is independently hydrogen or a C1-C3 alkyl group.

Aspect 65: The method of aspect 50, wherein the phenylindane dicarboxylic acid monomer has a structure represented by the formula:

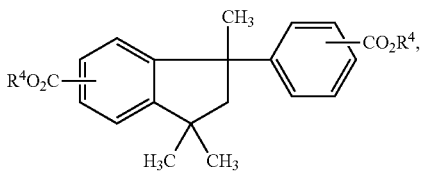

wherein wherein each $R^4$ is independently hydrogen or a C1-C3 alkyl group.

Aspect 66: The method of aspect 50, wherein the phenylindane dicarboxylic acid monomer is 3-(4-carboxyphenyl)-1,1,3-trimethyl-5-indan carboxylic acid, 3-(4-carboxyphenyl)-1,3-diethyl-1-methyl-5-indan carboxylic acid, or 3-(4-carboxyphenyl)-1,3-dipropyl-1-methyl-5-indan carboxylic acid.

Aspect 67: The method of aspect 50, wherein the phenylindane dicarboxylic acid monomer is this monomer is as 1,3, 3-trimethyl-1-phenylindan-4',5-dicarboxylic acid.

Aspect 68: The method of aspect 50, wherein the acid catalyzed conditions comprise reacting the alkylstyrene in the presence of hydrochloric acid, sulfuric acid or nitric acid, or a combination thereof.

Aspect 69: The method of aspect 50, wherein the acid catalyzed conditions or the metal catalyzed oxidation conditions comprise adjusting the temperature to at least about 40° C.

Aspect 70: The method of aspect 50, wherein the the acid catalyzed conditions or the metal catalyzed oxidation conditions comprise adjusting the temperature in the range of from about 40° C. to about 250° C.

Aspect 71: The method of aspect 50, wherein the acid catalyzed conditions or the metal catalyzed oxidation conditions comprise maintaining the reaction for at least about 1 hours.

Aspect 72: The method of aspect 50, further comprising reacting the first reaction product to provide a reaction product comprising at least one acetylated phenylindane.

Aspect 73: The method of aspect 72, wherein reacting is acetylating with an acetylating agent in the presence of a Friedel-Crafts catalyst to provide reaction product comprising an isomer mixture.

Aspect 74: The method of aspect 73, wherein the acetylating agent is acetyl chloride, chloroacetyl chloride or acetic anhydride, or a combination thereof.

Aspect 75: The method of aspect 73, wherein the Friedel-Crafts catalyst comprises aluminum chloride, zinc chloride, or iron(III) chloride, or a combination thereof.

Aspect 76: The method of aspect 72, wherein the acetylated phenylindane is diacetyl phenylindane.

Aspect 77: The method of aspect 50, wherein the metal catalyzed oxidation conditions comprise reacting the first reaction product in the presence of an oxidizing agent.

Aspect 78: The method of aspect 77, wherein the oxidizing agent comprises: chromic anhydride(CrO3); oxygen containing heavy metals comprising one or more of manganese, cobalt, lead, iron, nickel, copper, and vanadium; or oxides of one or more of manganese, cobalt, lead, iron, nickel, copper, and vanadium; or a combination thereof.

Aspect 79: The method of aspect 50, wherein the metal catalyzed oxidation conditions comprise reacting the first reaction product in the presence of $KMnO_4$ and pyridine.

Aspect 80: The method of aspect 50, wherein the first reaction product comprises at least about 50 wt % of phenylindane.

Aspect 81: The method of aspect 50, wherein the second reaction product comprises at least about 50 wt % of phenylindane dicarboxylic acid.

Aspect 82: The method of aspect 50, wherein the method provides a final yield of phenylindane dicarboxylic acid of at least about 60%.

Aspect 83: The method of aspect 50, further comprising purifying the second reaction product under conditions effective to provide a reaction product comprising at least 90 wt % phenylindane dicarboxylic acid.

Aspect 84: The method of aspect 83, further comprising the step of filtering, separating, washing, or drying, or a combination thereof.

Aspect 85: The method of aspect 84, wherein purifying comprises dissolving the reaction product using aqueous NaHCO3 solution or glacial acetic acid, or a combination thereof.

Aspect 86: The method of aspect 84, wherein purifying comprises adjusting the pH of reaction product to a pH effective to provide a solid reaction product.

Aspect 87: The method of aspect 50, further comprising separating of the second reaction product.

Aspect 88: The method of aspect 87, wherein the separating comprises chiral separation of the racemic mixture using high pressure liquid chromatography.

E. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Unless indicated otherwise, percentages referring to composition are in terms of wt %.

1. General Methods

All materials and reagents were used as is unless otherwise indicated.

In an aspect, thin-layer chromatography (TLC) analysis was performed using Hexane: Ethyl acetate (90:10) as eluent. Gas chromatography (GC) was performed using Shimadzu GC2010, instrument having auto injector, flame ionization detector (FID)

Column: HP-1 (30 m×0.53 mmID×1.5µ)
Injector Temp.: 300° C.
Detector Temp.: 300° C.
Flow: 2 ml/min; Split ratio: 1:20
Temperature: 60° C.-2 min-5° C./min-150° C.-3 min 20° C./min-300° C.-20 min
Column Flow: 4.92 ml/min
Carrier Gas: Helium In another aspect, high performance liquid chromatography (HPLC) was performed using Agilent 1100 Series auto injector instrument having photodiode array (PDA) detector, Column: Zorbax SB-C18 (4.6×150 mm, 5µ)
Injector Volume: 5 uL
Column oven Temp.: 40° C.
Flow: 1 ml/min
Wavelength: 240 nm
Mobile Phase: A: Water+0.1% ortho Phosphoric acid
C: Acetonitrile.

$^1$H NMR analysis was performed using Bruker 300 MHz instrument to perform $^1$H Nuclear Magnetic Resonance (NMR) spectral measurements with a solution of monomer in deuterated chloroform ($CDCl_3$) or deuterated dimethylsulphoxide (DMSO-d6) or deuterated methanol(CD3OD)

2. Synthesis of Intermediates/Compounds

Example 1

Conversion of Limonene to PIDA

In an aspect, limonene is used as a starting material in the synthesis of p-Cymene, which in-turn can be converted into p-Cresol and Terephthalic acid. Limonene can be dehydrogenated to p-Methyl,α-Methyl Styrene, which is then via a sequence of chemical reactions, including dimerization and oxidation, can be transformed into PIDA.

Example 2

PIDA Monomer from AMS Dimer

A dry reaction flask equipped with a magnetic stirrer, condenser, and nitrogen inlet was charged with 0.4 g concentrated $H_2SO_4$. To the reaction flask, 40 g alpha-methylstyrene was slowly added dropwise under $N_2$ atmosphere over a period of 1 hr with stirring. During addition, the temperature was maintained below 60° C. After the addition was completed, the temperature was slowly raised to 150° C. and maintained for 6 hrs. After completion of the reaction, the reaction mixture was cooled to room temperature. To the reaction, 100 ml deionized water was added, followed by ethyl acetate. Ethylacetate layer was evaporated to get AMS (alpha methyl styrene) dimer, which solidifies long standing with 90% HPLC purity.

Next, a 500 ml reaction flask equipped with a magnetic stirrer, condenser, and nitrogen inlet is charged with 190 ml CH2Cl2 and 30 g of AMS Dimer along with 22.89 g of acetylchloride. To this mixture 38 gm of anhydrous aluminum chloride was added maintaining 0-5° C. temperature. Stirred the reaction mixture at the same temperature for 1 hr, followed by refluxing for 6 hrs. The reaction mixture was then cooled to room temperature and poured to the ice-water. The organic layer was separated and dried over magnesium sulphate. The organic layer was concentrated under reduced pressure to get a required product as viscous mass having 90% HPLC purity.

To a 1 L three neck flask, charged with 500 ml of acetic acid, 24 g of Diacetyl AMS dimer and 125 gm of Ceric ammonium nitrate (CAN) were added at room temperature. The reaction mixture is stirred at 60° C. for 15 min and then at 90° C. for 15 min followed by reflux for 7 hrs. The dark orange color solution turns pale yellow solution. The reaction mixture is cooled and poured to ice-water to get a solid as required product. This solid is filtered and washed thoroughly with water and dried at 70° C., resulting in 93% HPLC purity.

Example 3

Bromination of p-Cymene Using KBrO3 and NaHSO3, Reagent system

Into a clean RB flask, p-Cymene (10 g, 0.0745 mol) was taken and into this added ethyl acetate (100 ml) followed by water (100 mL) and $KBrO_3$ (12.44 g, 0.0745 mol) and the resulting mixture was stirred at 25° C. for about 10 mins. Then into this slowly added a solution of $NaHSO_3$ (7.25 g, 0.0745 mol) in water (100 ml) for about 1 hr. The reaction mixture was then stirred at 25° C. for about 6 hrs. The layers were then separated; organic layer was washed with aq. Sodium thiosulphate solution and extracted with ethyl acetate (2×100 ml). Combined organic layer was dried over anhydrous sodium sulphate and concentrated under reduced pressure to give the crude product, which was then taken for further reaction without purification Dehydrohalogenation:

In a clean RB Flask, stage-I crude product (18.26 g) was taken and added n-heptane (80 ml) and the resulting solution was then heated to reflux for about 1 h. then cooled to room temperature and the solvent was evaporated under reduced pressure to give the crude product, which was then distilled under vacuum to give the dimethyl styrene along with unreacted p-cymene (8 g).

Dimerization Reaction:

A solution of mixture of dimethyl styrene and unreacted p-cymene (8 g) in n-heptane (30 ml) was slowly added into a mixture of Amberlyst-15 (690 mg) in n-heptane (60 ml) and the resultant mixture was then heated to reflux for about 1 h. After completion of the reaction as indicated by TLC, heating was stopped and the catalyst was filtered, washed with n-heptane (2×20 ml) and concentrated under reduced pressure to give the crude product. Crude product was then purified by vacuum distillation to give the pure dimer in good yield (6.47 g).

Oxidation of Dimer to PIDA:

In a clean RB flask, Dimer (6.2 g, 0.023 mol) was taken and added conc. $HNO_3$ (50%) 30 ml, and the resulting mixture was heated to reflux for about 43 h, then cooled to room temperature and the solid thus formed was filtered, washed with water and dried completely. To the crude product, 1 N NaOH solution (120 ml) was added followed by $KMnO_4$ (8 g) and the resultant mixture was then heated to reflux for about 1 hr. Then cooled to room temperature, acidified with conc. HCl (pH<2). The solid thus obtained was filtered, washed with water and dried to get PIDA (7.2 g).

Example 4

Reaction of p-Bromo Toluene

Synthesis of 8-hydroxy-p-cymene

In a clean RB flask, fitted with reflux condenser Mg (3.5 g, 0.1462 mol) was taken and added THF (125 ml) followed by slow addition of 4-bromo toluene (25 g, 0.1462 mol) for about 1 hr. The reaction mixture was then stirred at room temperature for about 3 h. Then into this slowly added acetone (10.7 mL, 0.1462 mol) and stirred at room temperature for about 2 hrs. After completion of the reaction as indicated by TLC, reaction mixture was then cooled to 0° C. and quenched with Sat ammonium chloride solution (30 ml) and extracted with ethyl acetate. Combined organic layer was dried over $Na_2SO_4$ and conc. Under reduced pressure to get the crude product (8-hydroxy p-cymene, 18.2 g).

Dimerization of 8-hydroxy-p-cymene

Procedure 1:
In a clean RB flask, toluene (16 ml) and Cocn. $H_2SO_4$ (7.5 ml) was taken and cooled to 0° C. Into this, slowly added a solution of 8-hydroxy-p-cymene (5 g, 0.033 mol) in toluene (4 ml) and the resulting mixture was then stirred at 0° C. for 45 mins. The reaction mixture was then diluted with water and extracted with toluene. Combined organic layer was washed with water (2×50 ml) and dried over anhydrous $Na_2SO_4$ and concentrated under reduced pressure to give the crude dimerized product (4.6 g).

Procedure 2:
In a clean RB flask fitted with closed distillation set up under 1 atm nitrogen pressure, Conc. $H_2SO_4$ (400 mg) was taken and into this slowly added 8-hydroxy-p-cymene (25 g) under 1 atm $N_2$ pressure by maintaining the temperature below 60° C. The temperature was then slowly raised to 150° C. and stirred at that temperature till the completion of the reaction. During the course of the reaction, the byproduct formed was collected along with the unreacted intermediate, with the help of distillation assembly. After completion of the reaction as indicated by TLC, reaction mixture was then cooled to room temperature and diluted with ethyl acetate (160 ml). Resulting mixture was then washed with brine solution (25 ml), followed by water (3×25 ml). Organic layer was separated and dried over anhydrous $Na_2SO_4$ and concentrated under reduced pressure to give the dimer in good yield (12.104 g, Purity by HPLC 92%).

Synthesis of α-p-dimethyl styrene

In a clean RB flask, fitted with reflux condenser Mg (3.5 g, 0.1462 mol) was taken and added THF (125 ml) followed by slow addition of 4-bromo toluene (25 g, 0.1462 mol) for about 1 hr. The reaction mixture was then stirred at room temperature for about 3 h. Then into this slowly added acetone (10.7 mL, 0.1462 mol) and stirred at room temperature for about 2 hrs. After completion of the reaction as indicated by TLC, reaction mixture was then cooled to 0° C. and quenched with 50% aqueous. $H_2SO_4$ solution (145 ml) and extracted with ethyl acetate. Combined organic layer was dried over $Na_2SO_4$ and conc. Under reduced pressure to get the crude product (α-p-dimethyl styrene, 14.92 g).

Dimerization of α-p-dimethyl styrene

Procedure 1:
In a clean RB flask, Amberlyst-15 (2.4 g) was taken and added n-heptane (100 ml) and stirred for 10 mins Into this slowly added a solution of α-p-dimethyl styrene (24 g, 0.1816 mol) in n-heptane (100 ml) and the resultant mixture was then heated to reflux for about 1 h. After completion of the reaction as indicated by TLC, reaction mixture was then cooled to room temperature; catalyst was then filtered and washed with n-heptane (2×50 ml). Combined filtrate was then concentrated under reduced pressure to give the crude product, which was then distilled under vacuum to give the pure dimer (22.90 g).

Procedure 2:
In a clean RB flask, Conc. $H_2SO_4$ (0.182 g) was taken and into this α-p-dimethyl styrene was slowly added by maintaining the temperature below 60° C. After completion of the addition, the temperature was then slowly raised to 150° C. and stirred till the completion of the reaction. After completion of the reaction, as indicated by TLC, reaction mixture was then cooled to room temperature, diluted with ethyl acetate (100 ml) and washed with brine solution (25 ml), followed by water (3×25 ml). Organic layer was separated, dried over anhydrous $Na_2SO_4$ and concentrated under reduced pressure to give the dimer in good yield (9.2 g).

Oxidation of Dimer to PIDA:
In a clean RB flask, Dimer (6.2 g, 0.023 mol) was taken and added conc. $HNO_3$ (50%) 30 ml, and the resulting mixture was heated to reflux for about 43 h, then cooled to room temperature and the solid thus formed was filtered, washed with water and dried completely. To the crude product, 1 N NaOH solution (120 ml) was added followed by $KMnO_4$ (8 g) and the resultant mixture was then heated to reflux for about 1 hr. Then cooled to room temperature, acidified with conc. HCl (pH<2). The solid thus obtained was filtered, washed with water and dried to get PIDA (7.2 g).

Example 5

A reaction flask equipped with stirrer, condenser and nitrogen inlet was charged with 80 ml of methyl magnesium bromide (3M solution in diethyl ether). The reaction mixture was then cooled to −5° C. using dry ice bath. 18 g of 4-methyl acetophenone, diluted with 100 ml of dry THF (Tetrahydrofuran) was added dropwise slowly, while maintaining vigorous stirring for 1 hour at below 10° C. The reaction mixture was slowly allowed to come to room temperature (20-25° C.), and stirred at this temperature for 6 hrs. After completion, the reaction mixture was cooled to 0° C. and 100 ml of ice cold water was added slowly over 1 hr, maintaining the temperature at 0-5° C. The pH was adjusted to 2-3 by adding 500 ml of 1M HCl very slowly over 1 hr, maintaining the temperature under 15° C., and stirred for 30 minutes. Next, 200 ml of Ethyl acetate was added and extracted three times. The organic layers were then separated, washed with 200 ml deionized water three times, and dried over sodium sulphate. After removal of the solvent at 45° C. under reduced pressure, the reaction product yielded 16 gm of crude product was analysed by GC (crude mixture has unreacted 4-methyl acetophenone, 80% GC purity of hydroxy cymene or carbinol, alpha-para dimethylstyrene, dimer). Crude product mixture was used as such without further purification for next step Alternatively, the Grignard reaction can also be quenched using Concentrated. HCl at 10-20° C. by adding acid slowly dropwise over a period of 1 hr to provide the corresponding alpha-para-dimethy styrene with 90% crude purity (HPLC).

A dry reaction flask, equipped with mechanical stirrer, distillation condenser and nitrogen inlet with 1 atmosphere pressure was charged with concentrated H2SO4. The 16 gm of crude product from above step was added as such slowly drop wise under N2 atmosphere over a period of 1 hr with stirring (controlling the temperature below 40° C.). After the addition, the temperature was slowly raised to 150° C. and maintained for 6 hrs. As reaction proceeds liberated water comes out from distillation setup, was collected. After reaction completion, the reaction mixture was cooled to room temperature, and 100 ml of deionized water was added, followed by 250 ml of ethyl acetate, and ethyl acetate layer separated. The aqueous layer washed with twice with 100 ml ethyl acetate. The ethyl acetate layers were combined, then washed three times with saturated sodium chloride solution, and four times with 200 ml of deionized water. The ethyl acetate layer was then dried over sodium sulfate, followed by removal of the solvent at 45° C. under reduced pressure to yield crude product having dimer (92% by GC purity) which was used as such without further purification for next step Alternatively, the Dimerization reaction can also be tried using 90% HPLC pure alpha-p-dimethylstyrene obtained from previous step directly by reacting it with Concentrated H2SO4 at 150° C. with out removing water (distillation), to yield dimer (90% HPLC pure) which was used as such for next step A dry, 3 necked reaction flasks, equipped with mechanical stirrer, condenser, and nitrogen inlet was charged with 450 ml of pyridine and 350 ml of deionized water. The crude dimer product from above step was then added with stirring. 35 gms of solid KMnO4 was added using powder funnel and heated to reflux for 1 hour. After 1 hr of stirring, another 35 gm of solid KMnO4 was added while maintaining the same temperature. Similarly, a final 35 gm of KMnO4 was added and stirred at 100° C. for 6 hours. After completion, the reaction mixture was cooled to room temperature, then 100 ml of deionized water was added, followed by concentrated HCl until a pH 2-3 was reached. 500 ml of ethyl acetate was added, and the ethyl acetate layer was separated. The aqueous layer was then washed twice with 250 ml ethyl acetate. The ethyl acetate layers were combined and washed with four times with 200 ml of deionized water. The ethyl acetate layer was then dried over sodium sulfate, and the solvent removed at 45° C. under reduced pressure to give a white to off-white, oxidized final product (85% HPLC purity), The product was confirmed by NMR (FIG. 1).

Example 6

Purification

A dry reaction flask, equipped with mechanical stirrer, condenser & nitrogen inlet was charged with 10 g of crude oxidized product (85% pure). 100 ml of freshly prepared 20% aqueous sodium bicarbonate solution was added until pH of 8 was reached, heated to 100° C., and stirred until completely dissolved. The solution was then filtered over celite bed at 50° C., and the clear filtrate was cooled to 25-30° C. (room temp). To the filtrate, 200 ml of ethyl acetate was added and the ethyl acetate layer separated five times, keeping the ethyl acetate layer aside. The aqueous layer was collected separately, and acidified to pH 2-3 using 1 M HCl to yield a solid white precipitate. The white solid (95% purity by HPLC) obtained was filtered, washed five times with 100 ml of deionized, and then dried at 100° C.

Figure 2:
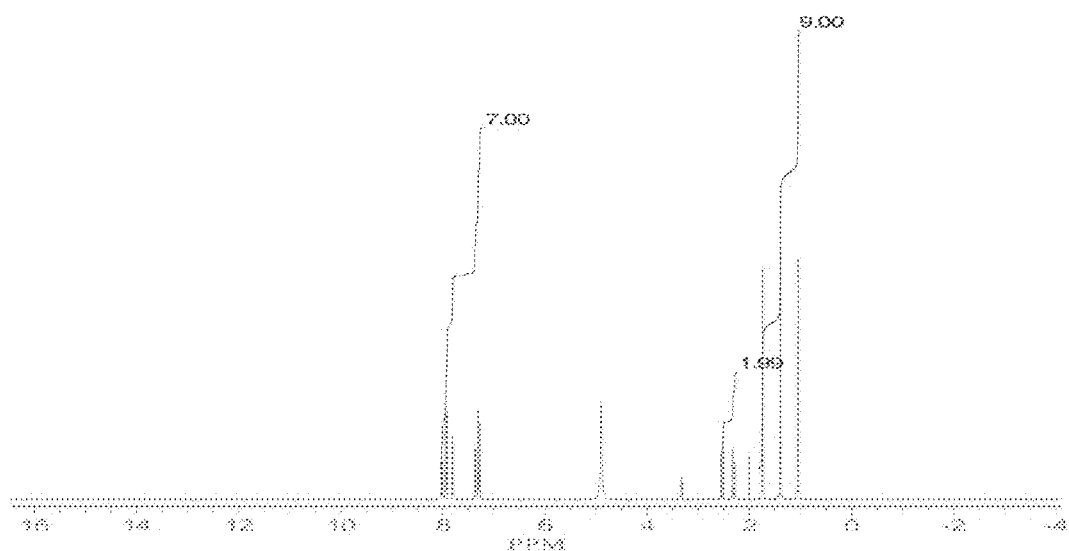
FIG. 2 shows representative NMR data of purified PIDA monomer prepared according to the present disclosure.
Figure 3:
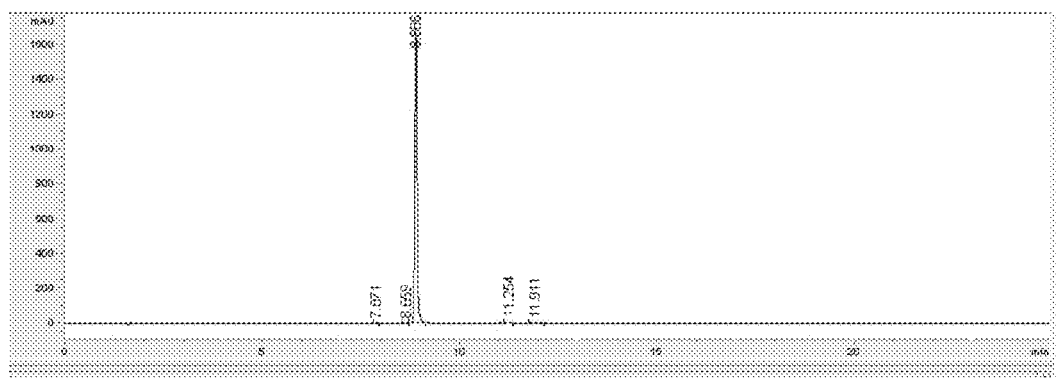
FIG. 3 shows representative HPLC data of purified PIDA monomer prepared according to the present disclosure.

A dry reaction flask, equipped with mechanical stirrer, condenser & nitrogen inlet was charged with 10 g of the white solid product (95% purity by HPLC). 200 ml of Glacial acetic acid was added, heated to 100° C., and stirred until completely dissolved. The solution was then filtered over celite bed at 70° C. The clear filtrate was then stirred at room temperature overnight to yield a white solid. The white solid obtained was then filtered, and washed with 10 ml of cold acetic acid. The filtrate was collected separately, while the obtained solid was washed five times with 100 ml of deionized, and then dried at 100° C. to yield 5 gm of white solid (99.5% purity by HPLC). The purified PIDA product was confirmed by NMR, purity by HPLC (FIGS. 2 and 3).

Example 7

Separation of Compounds

PIDA compounds were prepared as described herein. The racemic compounds were separated into their enantiomers, using chiral HPLC. The chiral HPLC was carried out under following general conditions:
  HPLC column: commercial available columns such as Daicel CHIRALPAK® IA, IC, ID or IF, Phenomenex Lux® Amylose-2, Lux® Cellulose-1, Supelco Astec® Cellulose DMP or its equivalent (e.g., 250×4, 6 mm, 5 µm)
  Mobile Phase: suitable solvents for particular monomer
  Wavelength: 254 nm or 280 nm
  Flow rate: 1 ml/min
  Sample: ~1 mg/ml in the mobile phase
  PIDA samples were dissolved in the mobile phase and run over different columns as described herein.

There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

The patentable scope of the disclosure is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A method for preparing a phenylindane dicarboxylic acid monomer, the method comprising:
  a) reacting an alkylstyrene under acid catalyzed conditions effective to provide a first reaction product comprising at least one C20 to C32 phenylindane; and b) reacting the first reaction product under a metal catalyzed oxidation conditions effective to provide a second reaction product comprising a racemic mixture including a phenylindane dicarboxylic acid monomer.

2. The method of claim 1, wherein the phenylindane dicarboxylic acid monomer does not exhibit a half maximal inhibitory concentration ($IC_{50}$) less than 0.00025M for alpha or beta in vitro estradiol receptors.

3. The method of claim 1, wherein the alkylstyrene has a structure represented by the formula:

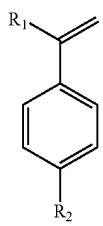

wherein each of R1 and R2 is each independently selected from hydrogen and C1-C3 alkyl.

4. The method of claim 1, wherein the alkylstyrene is alpha-methylstyrene.

5. The method of claim 1, wherein the alkylstyrene is α-p-dimethylstyrene.

6. The method of claim 1, wherein the phenylindane is trimethyl phenylindane.

7. The method of claim 1, wherein the phenylindane is tetramethyl phenylindane.

8. The method of claim 1, further comprising the step of reacting limonene to provide the the alkylstyrene.

9. The method of claim 1, further comprising the step of reacting an alkylbenzene to provide the alkylstyrene.

10. The method of claim 9, wherein the alkylbenzene is p-cymene or p-bromo toluene, or a combination thereof.

11. The method of claim 1, further comprising the step of reacting an acetophenone to provide the alkylstyrene.

12. The method of claim 11, wherein the acetophenone is reacted in the presence of a Grignard reagent.

13. The method of claim 12, wherein the Grignard reagant is methyl magnesium bromide.

14. The method of claim 1, wherein the phenylindane dicarboxylic acid monomer has a structure represented by the formula:

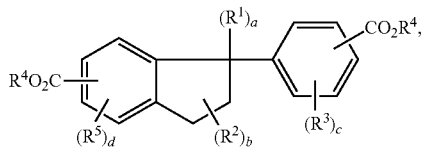

wherein $R^1$, $R^2$, $R^3$, and $R^5$ are each independently a C1-C3 alkyl group, a is 0-1, b is 0-4, c is 0-4 and d is 0-3, and each $R^4$ is independently a hydrogen or a C1-C3 alkyl group.

15. The method of claim 1, wherein the phenylindane dicarboxylic acid monomer has a structure represented by the formula

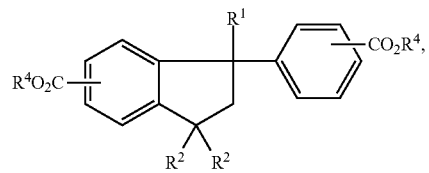

wherein each $R^4$ is independently hydrogen or a C1-C3 alkyl group.

16. The method of claim 1, wherein the phenylindane dicarboxylic acid monomer has a structure represented by the formula:

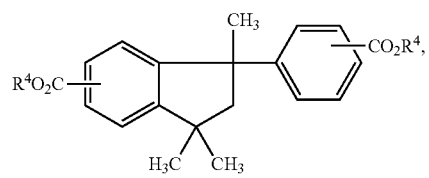

wherein wherein each $R^4$ is independently hydrogen or a C1-C3 alkyl group.

17. The method of claim 1, wherein the phenylindane dicarboxylic acid monomer is 3-(4-carboxyphenyl)-1,1,3-trimethyl-5-indan carboxylic acid, 3-(4-carboxyphenyl)-1,3-diethyl-1-methyl-5-indan carboxylic acid, or 3-(4-carboxyphenyl)-1,3-dipropyl-1-methyl-5-indan carboxylic acid.

18. The method of claim 1, wherein the phenylindane dicarboxylic acid monomer is this monomer is as 1,3,3-trimethyl-1-phenylindan-4',5-dicarboxylic acid.

19. The method of claim 1, wherein the acid catalyzed conditions comprise reacting the alkylstyrene in the presence of hydrochloric acid, sulfuric acid or nitric acid, or a combination thereof.

20. The method of claim 1, wherein the acid catalyzed conditions or the metal catalyzed oxidation conditions comprise adjusting the temperature to at least about 40° C.

21. The method of claim 1, wherein the the acid catalyzed conditions or the metal catalyzed oxidation conditions comprise adjusting the temperature in the range of from about 40° C. to about 250° C.

22. The method of claim 1, wherein the acid catalyzed conditions or the metal catalyzed oxidation conditions comprise maintaining the reaction for at least about 1 hours.

23. The method of claim 1, further comprising reacting the first reaction product to provide a reaction product comprising at least one acetylated phenylindane.

24. The method of claim 23, wherein reacting is acetylating with an acetylating agent in the presence of a Friedel-Crafts catalyst to provide reaction product comprising an isomer mixture.

25. The method of claim 24, wherein the acetylating agent is acetyl chloride, chloroacetyl chloride or acetic anhydride, or a combination thereof.

26. The method of claim 24, wherein the Friedel-Crafts catalyst comprises aluminum chloride, zinc chloride, or iron (III) chloride, or a combination thereof.

27. The method of claim 23, wherein the acetylated phenylindane is diacetyl phenylindane.

28. The method of claim 1, wherein the metal catalyzed oxidation conditions comprise reacting the first reaction product in the presence of an oxidizing agent.

29. The method of claim 28, wherein the oxidizing agent comprises: chromic anhydride(CrO3); oxygen containing heavy metals comprising one or more of manganese, cobalt, lead, iron, nickel, copper, and vanadium; or oxides of one or more of manganese, cobalt, lead, iron, nickel, copper, and vanadium; or a combination thereof.

30. The method of claim 1, wherein the metal catalyzed oxidation conditions comprise reacting the first reaction product in the presence of $KMnO_4$ and pyridine.

31. The method of claim 1, wherein the first reaction product comprises at least about 50 wt % of phenylindane.

32. The method of claim 1, wherein the second reaction product comprises at least about 50 wt % of phenylindane dicarboxylic acid.

33. The method of claim 1, wherein the method provides a final yield of phenylindane dicarboxylic acid of at least about 60%.

34. The method of claim 1, further comprising purifying the second reaction product under conditions effective to provide a reaction product comprising at least 90 wt % phenylindane dicarboxylic acid.

35. The method of claim 34, further comprising the step of filtering, separating, washing, or drying, or a combination thereof.

36. The method of claim 34, wherein purifying comprises dissolving the reaction product using aqueous NaHCO3 solution or glacial acetic acid, or a combination thereof.

37. The method of claim 34, wherein purifying comprises adjusting the pH of reaction product to a pH effective to provide a solid reaction product.

38. The method of claim 1, further comprising separating of the second reaction product.

39. The method of claim 38, wherein the separating comprises chiral separation of the racemic mixture using high pressure liquid chromatography.

40. A method for preparing a phenylindane dicarboxylic acid monomer, the method comprising:
a) reacting alphamethylstyrene under first reaction conditions effective to provide a first reaction product comprising at least one phenylindane;
b) acetylating the first reaction product in the presence of a Friedel-Crafts catalyst to provide second reaction product comprising an acetylated phenylindane; and
c) reacting the second reaction product under second reaction conditions effective to provide a second reaction product comprising at least one phenylindane dicarboxylic acid monomer.

41. A method for preparing a phenylindane dicarboxylic acid monomer, the method comprising:
a) reacting a alkylbenzene to provide a first reaction product comprising at least one alkylstyrene;
b) reacting the first reaction product under first reaction conditions effective to provide a second reaction product comprising at least one phenylindane; and
c) reacting the second reaction product under second reaction conditions effective to provide a second reaction product comprising at least one phenylindane dicarboxylic acid monomer.

* * * * *